(12) United States Patent
Wang

(10) Patent No.: US 7,529,629 B2
(45) Date of Patent: May 5, 2009

(54) COMPUTATIONAL METHODS AND SYSTEMS FOR MULTIDIMENSIONAL ANALYSIS

(75) Inventor: Yongdong Wang, Wilton, CT (US)

(73) Assignee: Cerno Bioscience LLC, Danbury, CT (US)

( * ) Notice: Subject to any disclaimer, the term of this patent is extended or adjusted under 35 U.S.C. 154(b) by 30 days.

(21) Appl. No.: 10/554,863

(22) PCT Filed: Apr. 28, 2004

(86) PCT No.: PCT/US2004/013097

§ 371 (c)(1),
(2), (4) Date: Oct. 28, 2005

(87) PCT Pub. No.: WO2004/097582

PCT Pub. Date: Nov. 11, 2004

(65) Prior Publication Data

US 2006/0288339 A1     Dec. 21, 2006

Related U.S. Application Data

(60) Provisional application No. 60/466,011, filed on Apr. 28, 2003, provisional application No. 60/466,012, filed on Apr. 28, 2003, provisional application No. 60/466,010, filed on Apr. 28, 2003.

(51) Int. Cl.
*G01N 31/00* (2006.01)
*G06F 19/00* (2006.01)

(52) U.S. Cl. .............................. 702/22; 435/4; 436/161; 702/85

(58) Field of Classification Search .................. 702/22, 702/23, 30, 27, 85, 89, 109, 180; 435/416, 435/7.1; 436/58, 89, 161; 250/228, 287, 250/306; 324/304, 309
See application file for complete search history.

(56) References Cited

U.S. PATENT DOCUMENTS

| | | | |
|---|---|---|---|
| 5,121,338 A | 6/1992 | Lodder | 702/30 |
| 5,131,998 A | 7/1992 | Jorgenson et al. | 210/93 |
| 5,496,460 A | 3/1996 | Jorgenson et al. | 204/604 |
| 5,538,897 A | 7/1996 | Yates, III et al. | 436/89 |

(Continued)

OTHER PUBLICATIONS

Y. Wang et al., Standardization of Second-Order Instruments, Anal. Chem., vol. 65, No. 9, pp. 1174-1180, May 1993.

(Continued)

*Primary Examiner*—John H Le
(74) *Attorney, Agent, or Firm*—David Aker

(57) ABSTRACT

A method for analyzing data obtained from at least one sample in a separation system (10, 50, 60) that has a capability for separating components of a sample containing more than one component as a function of at least two different variables including obtaining data representative of the at least one sample from the system, the data being expressed as a function of the two variables; forming a data stack (70, 74, 78, 82, 84) having successive levels, each level containing successive data representative of the at least one sample; forming a data array (R) representative of a compilation of all of the data in the data stack; and separating the data array into a series of matrixes. A chemical analysis system that operates in accordance with the method, and a medium having computer readable program code for causing the system to perform the method.

40 Claims, 11 Drawing Sheets

U.S. PATENT DOCUMENTS

| | | | | |
|---|---|---|---|---|
| 5,559,728 | A | 9/1996 | Kowalski et al. | 702/85 |
| 6,138,082 | A | 10/2000 | Wang et al. | 702/109 |
| 6,449,584 | B1 | 9/2002 | Bertrand et al. | 702/80 |
| 6,489,121 | B1 | 12/2002 | Skilling | 435/7.1 |
| 6,579,720 | B1 * | 6/2003 | Pidgeon et al. | 436/161 |
| 6,677,114 | B1 | 1/2004 | Schneider et al. | 435/4 |
| 6,701,254 | B1 | 3/2004 | Williams et al. | 702/22 |
| 6,983,213 | B2 | 1/2006 | Wang | 702/85 |
| 2003/0091976 | A1 * | 5/2003 | Boschetti et al. | 435/4 |
| 2004/0126892 | A1 * | 7/2004 | Bogomolov et al. | 436/161 |
| 2006/0217911 | A1 | 9/2006 | Wang | 702/85 |

OTHER PUBLICATIONS

E. Bezemer et al., Study of the Hydrolysis od a Sulfonylurea Herbicide Using Liquid Chromotography with Diode Array Detection and Mass Spectrometry by Three-Way Multivariate Curve Resolution-Alternating Least Squares Anal. Chem. Vo. 73, No. 18, pp. 4403-4409, Sep. 2001.

G. J. Opiteck et al., Comprehensive On-Line LC/LC/MS of Proteins, Anal. Chem. vol. 69, No. 8, pp. 1518-1524, Apr. 1997.

G. J. Opiteck et al., Two-Dimensional SEC/RPLC Coupled Mass Spectrometry for the Analysis of Peptides, Anal. Chem., vol. 69, No. 13, pp. 2283-2291, Jul. 1997.

S. P. Gygi et al., Protein analysis by mass spectrometry and sequence database searching: Tools for cancer research in the post-genomic era, Electrophoresis, vol. 20, pp. 310-319, 1999.

E. F. Petricoin III et al., Use of proteomic patterns in serum to identify ovarian cancer, The Lancet, vol. 359, pp. 572-577, Feb. 2002.

A. J. Link et al., Direct analysis of protein complexes using mass spectrometry, Nature Biotechnology, vol. 17, pp. 676-682, Jul. 1999.

M. P. Washburn et al., Large-scale analysis of the yeast proteome by multidimensional protein identification technology, Nature Biotechnology, vol. 19, pp. 242-247, Mar. 2001.

S. P. Gygi et al., Quantitative analysis of complex protein mixtures using isoptope-coded affinity tags, Nature Biotechnology, vol. 17, pp. 994-999, Oct. 1999.

C.M. Fleming et al., Second-order Calibration and Higher, Encyclopedia of Analytical Chemistry, pp. 1-29, 2000.

D. Bylund, Chemometric Tools for Enhanced Performance in Liquid Chromatography-Mass Spectrometry, Acta Universitatis Upsaliensis, Uppsala, 2001.

D. Bylund et al, Chromatographic Alignment by Warping and Dynamic Programming As a Pre-processing Tool for PARFAC Modelling of Liquid Chromatography-Mass Spectrometry Data, Jour of Chromatography, vol. 961, No. 2, pp. 237-244 Jul., 2002.

A. de Juan et al., Comparison of three-way resolution methods for non-trilinear chemical data sets, J. Chemometries, vol. 15, pp. 749-772, 2001.

Prazen et al., Standardization of Second-Order Chematographic Chromatographic/Spectroscopic Data for Optimum Chemical Analysis, Anal. Chem. vol. 70, No. 2, pp. 218-225, Jul. 1998.

* cited by examiner $$\underline{R}_j = \begin{bmatrix} \# & \cdots & \# \\ \cdot & & \cdot \\ \cdot & \cdots & \cdot \\ \cdot & & \cdot \\ \# & \cdots & \# \end{bmatrix} = \begin{bmatrix} \# & & & & \\ \# & \# & & & \\ & \# & O & \# & \\ & & O & \# & \\ & & & \# & \# \end{bmatrix} \begin{bmatrix} \# & \cdots & \# \\ \cdot & & \cdot \\ \cdot & \cdots & \cdot \\ \cdot & & \cdot \\ \# & \cdots & \# \end{bmatrix} \begin{bmatrix} \# & \# & & & \\ \# & \# & & & \\ & & \# & O & \\ & & O & \# & \\ & & & \# & \# \end{bmatrix}$$

$\underline{R}_j$  $A_j$  $\underline{R}_j$  $B_j$

FIG. 9

COMPUTATIONAL METHODS AND SYSTEMS FOR MULTIDIMENSIONAL ANALYSIS

This application claims priority from provisional application Ser. Nos. 60/466,010, 60/466,011 and 60/466,012, all filed on Apr. 28, 2003, all of which are incorporated herein in their entirety. This application also claims priority from U.S. application Ser. No. 10/689,313 filed on Oct. 20, 2003, the entire contents of which are also incorporated by reference herein.

BACKGROUND OF THE INVENTION

1. Field of the Invention

The present invention relates to chemical analysis systems. More particularly, it relates to systems that are useful for the analysis of complex mixtures of molecules, including large organic molecules such as proteins, environmental pollutants, and petrochemical compounds, to methods of analysis used therein, and to a computer program product having computer code embodied therein for causing a computer, or a computer and a mass spectrometer in combination, to affect such analysis. Still more particularly, it relates to such systems that have mass spectrometer portions.

2. Prior Art

The race to map the human genome in the past several years has created a new scientific field and industry named genomics, which studies DNA sequences to search for genes and gene mutations that are responsible for genetic diseases through their expressions in messenger RNAs (mRNA) and the subsequent coding of peptides which give rise to proteins. It has been well established in the field that, while the genes are at the root of many diseases including many forms of cancers, the proteins to which these genes translate are the ones that carry out the real biological functions. The identification and quantification of these proteins and their interactions thus serve as the key to the understanding of disease states and the development of new therapeutics. It is therefore not surprising to see the rapid shift in both the commercial investment and academic research from genes (genomics) to proteins (proteomics), after the successful completion of the human genome project and the identification of some 35,000 human genes in the summer of 2000. Different from genomics, which has a more definable end for each species, proteomics is much more open-ended as any change in gene expression level, environmental factors, and protein-protein interactions can contribute to protein variations. In addition, the genetic makeup of an individual is relatively stable whereas the protein expressions can be much more dynamic depending on various disease states and many other factors. In this "post genomics era," the challenges are to analyze the complex proteins (i.e., the proteome) expressed by an organism in tissues, cells, or other biological samples to aid in the understanding of the complex cellular pathways, networks, and "modules" under various physiological conditions. The identification and quantitation of the proteins expressed in both normal and diseased states plays a critical role in the discovery of biomarkers or target proteins.

The challenges presented by the fast-developing field of proteomics have brought an impressive array of highly sophisticated scientific instrumentation to bear, from sample preparation, sample separation, imaging, isotope labeling, to mass spectral detection. Large data arrays of higher and higher dimensions are being routinely generated in both industry and academia around the world in the race to reap the fruits of genomics and proteomics. Due to the complexities and the sheer number of proteins (easily reaching into thousands) typically involved in proteomics studies, complicated, lengthy, and painstaking physical separations are performed in order to identify and sometime quantify individual proteins in a complex sample. These physical separations create tremendous challenges for sample handling and information tracking, not to mention the days, weeks, and even months it typically takes to fully elucidate the content of a single sample.

While there are only about 35,000 genes in the human genome, there are an estimated 500,000 to 2,000,000 proteins in human proteome that could be studied both for general population and for individuals under treatment or other clinical conditions. A typical sample taken from cells, blood, or urine, for example, usually contains up to several thousand different proteins in vastly different abundances. Over the past decade, the industry has popularized a process that includes multiple stages in order to analyze the many proteins existing in a sample. This process is summarized in Table 1 with the following notable features:

TABLE 1

A Typical Proteomics Process: Time, Cost, and Informatics Needs

| Steps | Proteomics Process |
|---|---|
| Sample collection | Isolate proteins from biological samples such as blood, tissue, urine, etc. Instrument cost: minimal; Time: 1-3 hours Mostly liquid phase sample Need to track sample source/preparation conditions |
| Gel separation | Separate proteins spatially through gel electrophoresis to generate up to several thousand protein spots Instrument cost: $150K; Time: 24 hours Liquid into solid phase Need to track protein separation conditions and gel calibration information |
| Imaging and spot cutting | Image, analyze, identify protein spots on the gel with MW/pI calibration, and spot cutting. Instrument cost: $150K; Time: 30 sec/spot Solid phase Track protein spot images, image processing parameters, gel calibration parameters, molecular weights (MW) and pI's, and cutting records |
| Protein digestion | Chemically break down proteins into peptides Instrument cost: $50K; Time: 3 hours Solid to liquid phase Track digestion chemistry &reaction conditions |
| Protein Spotting or Sample preparation | Mix each digested sample with mass spectral matrix, spot on sample targets, and dry (MALDI) or sample preparation for LC/MS(/MS) Instrument cost: $50K; Time: 30 sec/spot Liquid to solid phase Track volumes &concentrations for samples/reagents |
| Mass spectral analysis | Measure peptide(s) in each gel spot directly (MALDI) or via LC/MS(/MS) Instrument: $200K-650K; Time: 1-10 sec/spot on MALDI or 30 min/spot on LC/MS(/MS) Solid phase on MALDI or liquid phase on LC/MS(/MS) Track mass spectrometer operation, analysis, and peak processing parameters |
| Protein database search | Search private/public protein databases to identify proteins based on unique peptides Instrument cost: minimal; Time: 1-60 sec/spot |
| Summary | Instrument cost: $600K-$1 M Time/sample: several days minimal | a. It could take up to several days or weeks or even months to complete the analysis of a single sample.
b. The bulky hardware system costs $600,000 to $1M with significant operating (labor and consumables), maintenance, and lab space cost associated with it.
c. This is an extremely tedious and complex process that includes several different robots and a few different types of instruments to essentially separate one liquid sample into hundreds to thousands of individual solid spots, each of which needs to be analyzed one-at-a-time through another cycle of solid-liquid-solid chemical processing.
d. It is not a small challenge to integrate these pieces/steps together for a rapidly changing industry, and as a result, there is not yet a commercial system that fully integrates and automates all these steps. Consequently, this process is fraught with human as well as machine errors.
e. This process also calls for sample and data tracking from all the steps along the way—not a small challenge even for today's informatics.
f. Even for a fully automated process with a complete sample and data tracking informatics system, it is not clear how these data ought to be managed, navigated, and most importantly, analyzed.
g. At this early stage of proteomics, many researchers are content with qualitative identification of proteins. The holy grail of proteomics is, however, both identification and quantification, which would open doors to exciting applications not only in the area of biomarker identification for the purpose of drug discovery but also for clinical diagnostics, as evidenced by the intense interest generated from a recent publication (Pertricoin, E. F. III et al., Lancet, Vol. 359, pp. 573-77, (2002)) on using protein profiles from blood samples for ovarian cancer diagnostics. The current process cannot be easily adapted for quantitative analysis due to the protein loss, sample contamination, or lack of gel solubility, although attempts have been made for quantitative proteomics with the use of complex chemical processes such as ICAT (isotope-coded affinity tags); a general approach to quantitation wherein proteins or protein digests from two different sample sources are labeled by a pair of isotope atoms, and subsequently mixed in one mass spectrometry analysis (Gygi, S. P. et al. *Nat. Biotechnol.* 17, 994-999 (1999)).

Isotope-coded affinity tags (ICAT) is a commercialized version of the approach introduced recently by the Applied Biosystems of Foster City, Calif. In this technique, proteins from two different cell pools are labeled with regular reagent (light) and deuterium substituted reagent (heavy), and combined into one mixture. After trypsin digestion, the combined digest mixtures are subjected to the separation by biotin-affinity chromatography to result in a cysteine-containing peptide mixture. This mixture is further separated by reverse phase HPLC and analyzed by data dependent mass spectrometry followed by database search.

This method significantly simplifies a complex peptide mixture into a cysteine-containing peptide mixture and allows simultaneous protein identification by SEQUEST database search and quantitation by the ratio of light peptides to heavy peptides. Similar to LC/LC/MS/MS, ICAT also circumvents insolubility problem, since both techniques digest whole protein mixture into peptide fragments before separation and analysis.

While very powerful, ICAT technique requires a multi-step process for labeling and pre-separation process, resulting in the loss of low abundant proteins with added reagent cost and further reducing the throughput for the already slow proteomic analysis. Since only cysteine-containing peptides are analyzed, the sequence coverage is typically quite low with ICAT. As is the case in typical LC/MS/MS experiment, the protein identification is achieved through the limited number of MS/MS analysis on hopefully signature peptides, resulting in only one and at most a few labeled peptides for ratio quantitation.

Liquid chromatography interfaced with tandem mass spectrometry (LC/MS/MS) has become a method of choice for protein sequencing (Yates Jr. et al., *Anal. Chem.* 67, 1426-1436 (1995)). This method involves a few processes including digestion of proteins, LC separation of peptide mixtures generated from the protein digests, MS/MS analysis of resulted peptides, and database search for protein identification. The key to effectively identify proteins with LC/MS/MS is to produce as many high quality MS/MS spectra as possible to allow for reliable matching during database search. This is achieved by a data-dependent scanning technique in a quadrupole or an ion trap instrument. With this technique, the mass spectrometer checks the intensities and signal to noise ratios of the most abundant ion(s) in a full scan MS spectrum and perform MS/MS experiments when the intensities and signal to noise ratios of the most abundant ions exceed a preset threshold. Usually the three most abundant ions are selected for the product ion scans to maximize the sequence information and minimize the time required, as the selection of more than three ions for MS/MS experiments would possibly result in missing other qualified peptides currently eluting from the LC to the mass spectrometer.

The success of LC/MS/MS for identification of proteins is largely due to its many outstanding analytical characteristics. Firstly, it is a quite robust technique with excellent reproducibility. It has been demonstrated that it is reliable for high throughput LC/MS/MS analysis for protein identification. Secondly, when using nanospray ionization, the technique delivers quality MS/MS spectra of peptides at sub-fentamole levels. Thirdly, the MS/MS spectra carry sequence information of both C-terminal and N-terminal ions. This valuable information can be used not only for identification of proteins, but also for pinpointing what post translational modifications (PTM) have occurred to the protein and at which amino acid reside the PTM take place.

For the total protein digest from an organism, a cell line, or a tissue type, LC/MS/MS alone is not sufficient to produce enough number of good quality MS/MS spectra for the identification of the proteins. Therefore, LC/MS/MS is usually employed to analyze digests of a single protein or a simple mixture of proteins, such as the proteins separated by two dimensional electrophoresis (2DE), adding a minimum of a few days to the total analysis time, to the instrument and equipment cost, and to the complexity of sample handling and the informatics need for sample tracking. While a full MS scan can and typically do contain rich information about the sample, the current LC/MS/MS methodology relies on the MS/MS analysis that can be afforded for only a few ions in the full MS scan. Moreover, electrospray ionization (ESI) used in LC/MS/MS has less tolerance towards salt concentrations from the sample, requiring rigorous sample clean up steps.

Identification of the proteins in an organism, a cell line, and a tissue type is an extremely challenging task, due to the sheer number of proteins in these systems (estimated at thousands or tens of thousands). The development of LC/LC/MS/MS technology (Link, A. J. et al. *Nat. Biotechnol.* 17, 676-682 (1999); Washburn, M. P. et al, *Nat. Biotechnol.* 19, 242-247 (2001)) is one attempt to meet this challenge by going after one extra dimension of LC separation. This approach begins with the digestion of the whole protein mixture and employs a strong cation exchange (SCX) LC to separate protein digests by a stepped gradient of salt concentrations. This separation usually takes 10-20 steps to turn an extremely complex protein mixture into a relatively simplified mixture. The mixtures eluted from the SCX column are further introduced into a reverse phase LC and subsequently analyzed by mass spectrometry. This method has been demonstrated to identify a large number of proteins from yeast and the microsome of human myeloid leukemia cells.

One of the obvious advantages of this technique is that it avoids insolubility problems in 2DE, as all the proteins are digested into peptide fragments which are usually much more soluble than proteins. As a result, more proteins can be detected and wider dynamic range achieved with LC/LC/MS/MS. Another advantage is that chromatographic resolution increases tremendously through the extensive 2D LC separation so that more high quality MS/MS spectra of peptides can be generated for more complete and reliable protein identification. The third advantage is that this approach is readily automated within the framework of current LC/MS system for potentially high throughput proteomic analysis.

The extensive 2D LC separation in LC/LC/MS/Ms, however, could take 1-2 days to complete. In addition, this technique alone is not able to provide quantitative information of the proteins identified and a quantitative scheme such as ICAT would require extra time and effort with sample loss and extra complications. In spite of the extensive 2D LC separation, there are still a significant number of peptide ions not selected for MS/MS experiments due to the time constraint between the MS/MS data acquisition and the continuous LC elution, resulting in low sequence coverage (25% coverage is considered as very good already). While recent development in depositing LC traces onto a solid support for later MS/MS analysis can potentially address the limited MS/MS coverage issue, it would introduce significantly more sample handling and protein loss and further complicate the sample tracking and information management tasks.

Matrix-Assisted Laser Desorption Ionization (MALDI) utilizes a focused laser beam to irradiate the target sample that is co-crystalized with a matrix compound on a conductive sample plate. The ionized molecules are usually detected by a time of flight (TOF) mass spectrometer, due to their shared characteristics as pulsed techniques.

MALDI/TOF is commonly used to detect 2DE separated intact proteins because of its excellent speed, high sensitivity, wide mass range, high resolution, and contaminant-forgivingness. MALDI/TOF with capabilities of delay extraction and reflecting ion optics can achieve impressive mass accuracy at 1-10 ppm and mass resolution with m/$\Delta$m at 10000-15000 for the accurate analysis of peptides. However, the lack of MS/IS capability in MALDI/TOF is one of the major limitations for its use in proteomics applications. Post Source Decay (PSD) in MALDI/TOF does generate sequence-like MS/MS information for peptides, but the operation of PSD often is not as robust as that of a triple quadrupole or an ion trap mass spectrometer. Furthermore, PSD data acquisition is difficult to automate as it can be peptide-dependent.

The newly developed MALDI TOF/TOF system (Rejtar, T. et al., *J. Proteomr. Res.* 1(2) 171-179 (2002)) delivers many attractive features. The system consists of two TOFs and a collision cell, which is similar to the configuration of a tandem quadrupole system. The first TOF is used to select precursor ions that undergo collisional induced dissociation (CID) in the cell to generate fragment ions. Subsequently, the fragment ions are detected by the second TOF. One of the attractive features is that TOF/TOF is able to perform as many data dependent MS/MS experiments as necessary, while a typical LC/MS/MS system selects only a few abundant ions for the experiments. This unique development makes it possible for TOF/TOF to perform industry scale proteomic analysis. The proposed solution is to collect fractions from 2D LC experiments and spot the fractions onto an MALDI plate for MS/MS. As a result, more MS/MS spectra can be acquired for more reliable protein identification by database search as the quality of MS/MS spectra generated by high-energy CID in TOF/TOF is far better than PSD spectra.

The major drawback for this approach is the high cost of the instrument ($750,000), the lengthy 2D separations, the sample handling complexities with LC fractions, the cumbersome sample preparation processes for MALDI, the intrinsic difficulty in quantification with MALDI, and the huge informatics challenges for data and sample tracking. Due to the LC separation and the sample preparation time required, the analysis of several hundred proteins in one sample would take at least 2 days.

It is well recognized that Fourier-Transform Ion-Cyclotron Resonance (FTICR) MS is a powerful technique that can deliver high sensitivity, high mass resolution, wide mass range, and high mass accuracy. Recently, FTICR/MS coupled with LC showed impressive capabilities for proteomic analysis through Accurate Mass Tags (AMT) (Smith, R. D. et al, *Proteomics*, 2, 513-523 (2002)). AMT is such an accurate m/z value of a peptide that can be used to exclusively identify a protein. It has been demonstrated that, using the AMT approach, a single LC/FTICR-MS analysis can potentially identify more than $10^5$ proteins with mass accuracy of better than 1 ppm. Nonetheless, ATM alone may not be sufficient to pinpoint amino acid residue specific post-translational modifications of peptides. In addition, the instrument is prohibitively expensive at a cost of $750K or more with high maintenance requirements.

Protein arrays and protein chips are emerging technologies (Issaq, H. J. et al, *Biochem Biophys Res Commun.* 292(3), 587-592 (2002)) similar in the design concept to the oligonucleotide-chip used in gene expression profiling. Protein arrays consist of protein chips which contain chemically (cationic, anionic, hydrophobic, hydrophilic, etc.) or biochemically (antibody, receptor, DNA, etc.) treated surfaces for specific interaction with the proteins of interest. These technologies take advantages of the specificity provided by affinity chemistry and the high sensitivity of MADLI/TOF and offer high throughput detection of proteins. In a typical protein array experiment, a large number of protein samples can be simultaneously applied to an array of chips treated with specific surface chemistries. By washing away undesired chemical and biomolecular background, the proteins of interest are docked on the chips due to affinity capturing and hence "purified". Further analysis of individual chip by MALDI-TOF results in the protein profiles in the samples. These technologies are ideal for the investigation of protein-protein interactions, since proteins can be used as affinity reagents to treat the surface to monitor their interaction with other specific proteins. Another useful application of these technologies is to generate comparative patterns between normal and diseased tissue samples as a potential tool for disease diagnostics.

Due to the complicated surface chemistries involved and the added complications with proteins or other protein-like binding agents such as denaturing, folding, and solubility issues, protein arrays and chips are not expected to have as wide an application as gene chips or gene expression arrays.

Thus, the past 100 years have witnessed tremendous strides made on the MS instrumentation with many different types of instruments designed and built for high throughput, high resolution, and high sensitivity work. The instrumentation has been developed to a stage where single ion detection can be routinely accomplished on most commercial MS systems with unit mass resolution allowing for the observation of ion fragments coming from different isotopes. In stark contrast to the sophistication in hardware, very little has been done to systematically and effectively analyze the massive amount of MS data generated by modern MS instrumentation.

In a typical mass spectrometer, the user is usually required or supplied with a standard material having several fragment ions covering the mass spectral m/z range of interest. Subject to baseline effects, isotope interferences, mass resolution, and resolution dependence on mass, peak positions of a few ion fragments are determined either in terms of centroids or peak maxima through a low order polynomial fit at the peak top. These peak positions are then fit to the known peak positions for these ions through either $1^{st}$ or other higher order polynomial fit to calibrate the mass (m/z) axis.

After the mass axis calibration, a typical mass spectral data trace would then be subjected to peak analysis where peaks (ions) are identified. This peak detection routine is a highly empirical and compounded process where peak shoulders, noise in data trace, baselines due to chemical backgrounds or contamination, isotope peak interferences, etc., are considered.

For the peaks identified, a process called centroiding is typically applied to attempt to calculate the integrated peak areas and peak positions. Due to the many interfering factors outlined above and the intrinsic difficulties in determining peak areas in the presence of other peaks and/or baselines, this is a process plagued by many adjustable parameters that can make an isotope peak appear or disappear with no objective measures of the centroiding quality.

Thus, despite their apparent sophistication current approaches have several pronounced disadvantages. These include:

Lack of Mass Accuracy. The mass calibration currently in use usually does not provide better than 0.1 amu (m/z unit) in mass determination accuracy on a conventional MS system with unit mass resolution (ability to visualize the presence or absence of a significant isotope peak).

In order to achieve higher mass accuracy and reduce ambiguity in molecular fingerprinting such as peptide mapping for protein identification, one has to switch to an MS system with higher resolution such as quadrupole TOF (qTOF) or FT ICR MS which come at significantly higher cost.

Large Peak Integration Error. Due to the contribution of mass spectral peak shape, its variability, the isotope peaks, the baseline and other background signals, and the random noise, current peak area integration has large errors (both systematic and random errors) for either strong or weak mass spectral peaks.

Difficulties with Isotope Peaks. Current approach does not have a good way to separate the contributions from various isotopes which usually give out partially overlapped mass spectral peaks on conventional MS systems with unit mass resolution. The empirical approaches used either ignore the contributions from neighboring isotope peaks or over-estimate them, resulting in errors for dominating isotope peaks and large biases for weak isotope peaks or even complete ignorance of the weaker peaks. When ions of multiple charges are concerned, the situation becomes worse even, due to the now reduced separation in mass unit between neighboring isotope peaks.

Nonlinear Operation. The current approaches use a multistage disjointed process with many empirically adjustable parameters during each stage. Systematic errors (biases) are generated at each stage and propagated down to the later stages in an uncontrolled, unpredictable, and nonlinear manner, making it impossible for the algorithms to report meaningful statistics as measures of data processing quality and reliability.

Dominating Systematic Errors. In most of MS applications, ranging from industrial process control and environmental monitoring to protein identification or biomarker discovery, instrument sensitivity or detection limit has always been a focus and great efforts have been made in many instrument systems to minimize measurement error or noise contribution in the signal. Unfortunately, the peak processing approaches currently in use create a source of systematic error even larger than the random noise in the raw data, thus becoming the limiting factor in instrument sensitivity or reliability.

Mathematical and Statistical Inconsistency. The many empirical approaches used currently make the whole mass spectral peak processing inconsistent either mathematically or statistically. The peak processing results can change dramatically on slightly different data without any random noise or on the same synthetic data with slightly different noise. In order words, the results of the peak processing are not robust and can be unstable depending on the particular experiment or data collection.

Instrument-To-Instrument Variations. It has usually been difficult to directly compare raw mass spectral data from different MS instruments due to variations in the mechanical, electromagnetic, or environmental tolerances. With the current ad hoc peak processing applied on the raw data, it only adds to the difficulty of quantitatively comparing results from different MS instruments. On the other hand, the need for comparing either raw mass spectral data directly or peak processing results from different instruments or different types of instruments has been increasingly heightened for the purpose of impurity detection or protein identification through the searches in established MS libraries.

A second order instrument generates a matrix of data for each sample and can have a higher analytical power than first order instruments if the data matrix is properly structured. The most widely used proteomics instrument, LC/MS, is a typical example of second order instrument capable of potentially much higher analytical power than what is currently achieved. Other second order proteomics instruments include LC/LC with single UV wavelength detection, 1D gel with MALDI-TOF MS detection, 1D protein arrays with MALDI MS detection, etc.

Two-dimensional gel electrophoresis (2D gel) has been widely used in the separation of proteins in complex biological samples such as cells or urines. Typically the spots formed by the proteins are stained with silver for easy identification with visible imaging systems. These spots are subsequently excised, dissolved/digested with enzymes, transported onto MALDI targets, dried, and analyzed for peptide signatures using MALDI time-of-flight mass spectrometer.

Several complications arise from this process:

1. The protein spots are not guaranteed to contain only single proteins, especially at extreme ends of the separation parameters (pI for charge or MW for molecular weight). This usually makes peptide searching difficult if not impossible. Additional liquid chromatography separation may be required for each excised spot, which further slows down the analysis.
2. The conversion of biological sample from liquid phase to solid phase (on the gel), back into liquid phase (for digestion), and finally into solid phase again (for MALDI TOF analysis) is a very cumbersome process prone to errors, carry-overs, and contaminations.

3. Due to the sample conversion processes involved and the fact the MALDI-TOF irreproducibility in sampling and ionization, this analysis has been widely recognized as only qualitative and not quantitative.

Thus, in spite of its tremendous potential and clear advantages over first and zeroth order analysis, second order instrument and analysis have so far been limited to academia research where the sample is composed of a few synthetic analytes with no sign of commercialization. There are several barriers that must be crossed in order for this approach to reach its huge potential. These include:

a. In second order protein analysis, it is even more important to use raw profile MS scans instead of the centroid data currently used in virtually all MS applications. To maintain the bilinear data structure, successive MS scans of a particular ion eluting from LC needs to have the same mass spectral peak shape (obviously at different peak heights), a critical second order structure destroyed by centroiding and de-isotoping (summing all isotope peaks into one integrated area).

The sticks from centroiding data appear at different mass locations (up to 0.5 amu error) from successive MS scans of the same ion.

b. Higher order instrument and analysis requires more robust instrument and measurement process and artifacts such as shifts in one or two of the dimensions can severely compromise the quantitative and even the qualitative results of the analysis (Wang, Y. et al, *Anal. Chem.* 63, 2750 (1991); Wang, Y. et al, *Anal. Chem.*, 65, 1174 (1993); Kiers, H. A. L. et al, *J. Chemometrics* 13, 275 (1999)), in spite of the recent progress made in academia (Bro, R. et al, *J. Chemometrics* 13, 295 (1999)). Other artifacts such as non-linearity or non-bilinearity could also lead to complications (Wang, Y. et al, *J. Chemometrics*, 7, 439 (1993)). Standardization and algorithmic corrections need to be developed in order to maintain the bilinearity of second order proteomics data.

c. In many MS instruments such as quadrupole MS, the mass spectral scan time is not negligible compared to the protein or peptide elution time. Therefore, a significant skew would exist where the ions measured in one mass spectral scan comes from different time points during the LC elution, similar to what has been reported for GC/MS (Stein, S. E. et al, *J. Am. Soc. Mass Spectrom.* 5, 859 (1994)).

Thus, there exists a significant gap between where the proteomics research would like to be and where it is at the present.

SUMMARY OF THE INVENTION

It is an object of the invention to provide a chemical analysis system, which may include a mass spectrometer, and a method for operating a chemical analysis system that overcomes the disadvantages described above.

It is another object of the invention to provide a storage media having thereon computer readable program code for causing a chemical analysis, including a chemical analysis system having a mass spectrometer, system to perform the method in accordance with the invention.

These objects and others are achieved in accordance with a first aspect of the invention by using 2D gel imaging data acquired from intact proteins to perform both qualitative and quantitative analysis without the use of mass spectrometer in the presence of protein spot overlaps. In addition the invention facilitates direct quantitative comparisons between many different samples collected over either a wider population range (diseased and healthy), over a period of time on the same population (development of disease), and over different treatment methods (response to potential treatment), etc. The gel spot alignment and matching are automatically built into the data analysis to yield the best overall results. The approach in accordance with the invention represents a fast, inexpensive, quantitative, and qualitative tool for both protein identification and protein expression analysis.

Generally, the invention is directed to a method for analyzing data obtained from at least one sample in a separation system that has a capability for separating components of a sample containing more than one component as a function of at least two different variables, the method comprising obtaining data representative of the at least one sample from the system, the data being expressed as a function of the two variables; forming a data stack having successive levels, each level containing successive data representative of the at least one sample; forming a data array representative of a compilation of all of the data in the data stack; and separating the data array into a series of matrixes, the matrixes being: a concentration matrix representative of concentration of each component in the sample; a first profile of the components as a function of a first of the variables; and a second profile of the components as a function of a second of the variables. There may be only one, or a single sample, and the successive data is representative of the sample as a function of time. Successive data may be representative of the single sample as a function of mass of its components. Alternatively, there may be a plurality of samples, and the successive data is then representative of successive samples.

The invention is more specifically directed to a method for analyzing data obtained from multiple samples in a separation system that has a capability for separating components of a sample containing more than one component as a function of two different variables, the method comprising obtaining data representative of multiple samples from the system, the data being expressed as a function of the two variables; forming a data stack having successive levels, each level containing one of the data samples; forming a data array representative of a compilation of all of the data in the data stack; and separating the data array into a series of matrixes, the matrixes being: a concentration matrix representative of concentration of each component in the sample; a first profile of the components as a function of the first variable; and a second profile of the components as a function of the second variable. The first profile and the second profile are representative of profiles of substantially pure components. The method further comprises performing qualitative analysis using at least one of the first profile and the second profile.

The method may further comprise standardizing data representative of a sample by performing a data matrix multiplication of such data into the product of a first standardization matrix, the data itself, and a second standardization matrix, to form a standardized data matrix. Terms in the first standardization matrix and the second standardization matrix may have values that cause the data to be represented at positions with respect to the two variables, which are different in the standardized data matrix from those in the data array. The first standardization matrix shifts the data with respect to the first variable, and the second standardization matrix shifts the data with respect to the second variable. Terms in the first standardization matrix and the second standardization matrix have values that serve to standardize distribution shapes of the data with respect to the first and second variable, respectively. Terms in the first standardization matrix and the second standardization matrix may be determined by applying a sample having known components to the apparatus; and selecting terms for the first standardization matrix and the second standardization matrix which cause data produced by the known components to be positioned properly with respect to the first variable and the second variable. The terms may be determined by selecting terms which produce a smallest error in position of the data with respect to the first variable and the second variable in the standardized data matrix. The term of the first standardization matrix and the second standardization matrix are preferably computed for each sample, and so as to produce a smallest error over all samples. At least one of the first and second standardization matrices can be simplified to be either a diagonal matrix or an identity matrix. The terms in the first standardization matrix and the second standardization matrix may be based on parameterized known functional dependence of the terms on the variables.

Values of terms in the first standardization matrix and the second standardization matrix are determined by solving the data array R:

$$R = C \cdot I \cdot W + E$$

where Q (m×k) contains pure profiles of all k components with respect to the first variable, W (n×k) contains pure profiles with respect to the second variable for the components, C (p×k) contains concentrations of these components in all p samples, I is a new data array with scalars on its super-diagonal as the only nonzero elements, and E (m×n×p) is a residual data array.

The separation apparatus may be a two-dimensional electrophoresis separation system, wherein the first variable is isoelectric point and the second variable is molecular weight.

The variables may be a result of any combination, in no particular sequence, and including self-combination, of chromatographic separation, capillary electrophoresis separation, gel-based separation, affinity separation and antibody separation.

The two variables may be mass associated with the mass axis of a mass spectrometer.

The apparatus may further comprise a chromatography system for providing the samples to the mass spectrometer, retention time being another of the two variables.

The apparatus may further comprise an electrophoresis separation system for providing the samples to the mass spectrometer, migration characteristics of the sample being another of the two variables.

In the method the data is preferably continuum mass spectral data. Preferably, the data is used without centroiding. The data may be corrected for time skew. Preferably, a calibration of the data with respect to mass and mass spectral peak shapes is performed.

One of the first variable and the second variable may be that of a region on a protein chip having a plurality of protein affinity regions.

The method may further comprise obtaining data for the data array by using a single channel analyzer and by analyzing the samples successively. The single channel detector may be based on one of light absorption, light emission, light reflection, light transmission, light scattering, refractive index, electrochemistry, conductivity, radioactivity, or any combination thereof. The components in the sample may be bound to at least one of fluorescence tags, isotope tags, stains, affinity tags, or antibody tags.

The invention is also directed to a computer readable medium having thereon computer readable code for use with a chemical analysis system having a data analysis portion for analyzing data obtained from multiple samples, the chemical analysis system having a separation portion that has a capability for separating components of a sample containing more than one component as a function of two different variables, the computer readable code being for causing the computer to perform a method comprising obtaining data representative of multiple samples from the system, the data being expressed as a function of the two variables; forming a data stack having successive levels, each level containing one of the data samples; forming a data array representative of a compilation of all of the data in the data stack; and separating the data array into a series of matrixes, the matrixes being: a concentration matrix representative of concentration of each component in the sample; a first profile of the components as a function of the first variable; and a second profile of the components as a function of the second variable. The computer readable medium may further comprise computer readable code for causing the computer to analyze data by performing the steps of any one of the methods stated above.

The invention is further directed to a chemical analysis system for analyzing data obtained from multiple samples, the system having a separation system that has a capability for separating components of a sample containing more than one component as a function of two different variables, the system having apparatus for performing a method comprising obtaining data representative of multiple samples from the system, the data being expressed as a function of the two variables; forming a data stack having successive levels, each level containing one of the data samples; forming a data array representative of a compilation of all of the data in the data stack; and separating the data array into a series of matrixes, the matrixes being: a concentration matrix representative of concentration of each component in the sample; a first profile of the components as a function of the first variable; and a second profile of the components as a function of the second variable. The chemical analysis system may have facilities for performing the steps of any of the methods described above.

The invention further includes a method for analyzing data obtained from a sample in a separation system that has a capability for separating components of a sample containing more than one component, the method comprising separating the sample with respect to at least a first variable to form a separated sample; separating the separated sample with respect to at least a second variable to form a further separated sample; obtaining data representative of the further separated sample from a multi-channel analyzer, the data being expressed as a function of three variables; forming a data stack having successive levels, each level containing data from one channel of the multi-channel analyzer; forming a data array representative of a compilation of all of the data in the data stack; and separating the data array into a series of matrixes or arrays, the matrixes or arrays being: a concentration data array representative of concentration of each component in the sample on its super-diagonal; a first profile of each component as a function of a first variable; a second profile of each component as a function of a second variable; and a third profile of each component as a function of a third variable. The first profile, the second profile, and the third profile are representative of profiles of substantially pure components. The method further comprises performing qualitative analysis using at least one of the first profile, the second profile, and the third profile.

The method further comprises standardizing data representative of a sample by performing a data matrix multiplication of such data into the product of a first standardization matrix, the data itself, and a second standardization matrix, to form a standardized data matrix. Terms in the first standardization matrix and the second standardization matrix have values that cause the data to be represented at positions with respect to two of the three variables, which are different in the standardized data matrix from those in the data array. The first standardization matrix shifts the data with respect to one of the two variables, and the second standardization matrix shifts the data with respect to the other of the two variables. Terms in the first standardization matrix and the second standardization matrix may have values that serve to standardize distribution shapes of the data with respect to the two variables, respectively. Terms in the first standardization matrix and the second standardization matrix are determined by applying a sample having known components to the apparatus; and selecting terms for the first standardization matrix and the second standardization matrix which cause data produced by the known components to be positioned properly with respect to the two variables.

The terms are determined by selecting terms that produce a smallest error in position of the data with respect to the two variables, in the standardized data matrix. The terms of the first standardization matrix and the second standardization matrix may be computed for a single channel. The terms of the first standardization matrix and the second standardization matrix are computed so as to produce a smallest error for the channel.

At least one of the first and second standardization matrices can be simplified to be either a diagonal matrix or an identity matrix. Preferably, the terms in the first standardization matrix and the second standardization matrix are based on parameterized known functional dependence of the terms on the variables.

In accordance with the invention, the values of terms in the first standardization matrix and in the second standardization matrix are determined by solving data array R:

$$R = Q \cdot I \cdot W \cdot C + E$$

where Q (m×k) contains pure profiles of all k components with respect to the first variable, W (n×k) contains pure profiles with respect to the second variable for the components, C (p×k) contains pure profiles of these components with respect to the multichannel detector or the third variable, I (k×k×k) is a new data array with scalars on its super-diagonal as the only nonzero elements representing the concentrations of all the k components, and E (m×n×p) is a residual data array.

The separation apparatus used may be a one-dimensional electrophoresis separation system, wherein the variable is one of isoelectric point and molecular weight.

The two separation variables may be a result of any combination, in no particular sequence, and including self-combination, of chromatographic separation, capillary electrophoresis separation, gel-based separation, affinity separation and antibody separation One of the three variables may be mass associated with the mass axis of a mass spectrometer.

The apparatus used may comprise at least one chromatography system for providing the separated samples to the mass spectrometer, retention time being at least one of the variables. The apparatus may also comprise at least one electrophoresis separation system for providing the separated samples to the mass spectrometer, migration characteristics of the sample being at least one of the variables. Preferably, the data is continuum mass spectral data. Preferably the data is used without centroiding.

The method may further comprise correcting the data for time skew. The method also may further comprise performing a calibration of the data with respect to mass and spectral peak shapes.

The apparatus used may comprise a protein chip having a plurality of protein affinity regions, location of a region being one of the three variables.

The multi-channel analyzer used may be based on one of light absorption, light emission, light reflection, light transmission, light scattering, refractive index, electrochemistry, conductivity, radioactivity, or any combination thereof. The components in the sample may be bound to at least one of fluorescence tags, isotope tags, stains, affinity tags, or antibody tags.

The apparatus used may comprise a two-dimensional electrophoresis separation system, wherein a first of the at least one variable is isoelectric point and a second of the at least one variable is molecular weight.

The invention is also directed to a computer readable medium having thereon computer readable code for use with a chemical analysis system having a data analysis portion for analyzing data obtained from a sample, the chemical analysis system having a separation portion that has a capability for separating components of a sample containing more than one component as a function of at least one variable, the computer readable code being for causing the computer to perform a method comprising separating the sample with respect to at least a first variable to form a separated sample; separating the separated sample with respect to at least a second variable to form a further separated sample; obtaining data representative of the further separated sample from a multi-channel analyzer, the data being expressed as a function of three variables; forming a data stack having successive levels, each level containing data from one channel of the multi-channel analyzer; forming a data array representative of a compilation of all of the data in the data stack; and separating the data array into a series of matrixes or arrays, the matrixes or arrays being: a concentration data array representative of concentration of each component in the sample on its super-diagonal; a first profile of each component as a function of a first variable; a second profile of each component as a function of a second variable; and a third profile of each component as a function of a third variable. The computer readable medium may further comprise computer readable code for causing the computer to analyze data by performing the steps of any of the methods set forth above.

The invention is also directed to a chemical analysis system for analyzing data obtained from a sample, the system having a separation system that has a capability for separating components of a sample containing more than one component as a function of at least one variable, the system having apparatus for performing a method comprising separating the sample with respect to at least a first variable to form a separated sample; separating the separated sample with respect to at least a second variable to form a further separated sample; obtaining data representative of the further separated sample from a multi-channel analyzer, the data being expressed as a function of three variables; forming a data stack having successive levels, each level containing data from one channel of the multi-channel analyzer; forming a data array representative of a compilation of all of the data in the data stack; and separating the data array into a series of matrixes or arrays, the matrixes or arrays being: a concentration data array representative of concentration of each component in the sample on its super-diagonal; a first profile of each component as a function of a first variable; a second profile of each component as a function of a second variable; and a third profile of each component as a function of a third variable. The chemical analysis system may further comprise facilities for performing the steps of the methods described above.

BRIEF DESCRIPTION OF THE DRAWINGS

The foregoing aspects and other features of the present invention are explained in the following description, taken in connection with the accompanying drawings, wherein like numerals indicate like components, and wherein:

FIG. 9 illustrates a transformation for automatic alignment of separation axes and corresponding profiles, in accordance with the invention.

DETAILED DESCRIPTION OF THE PREFERRED EMBODIMENT

Figure 1:
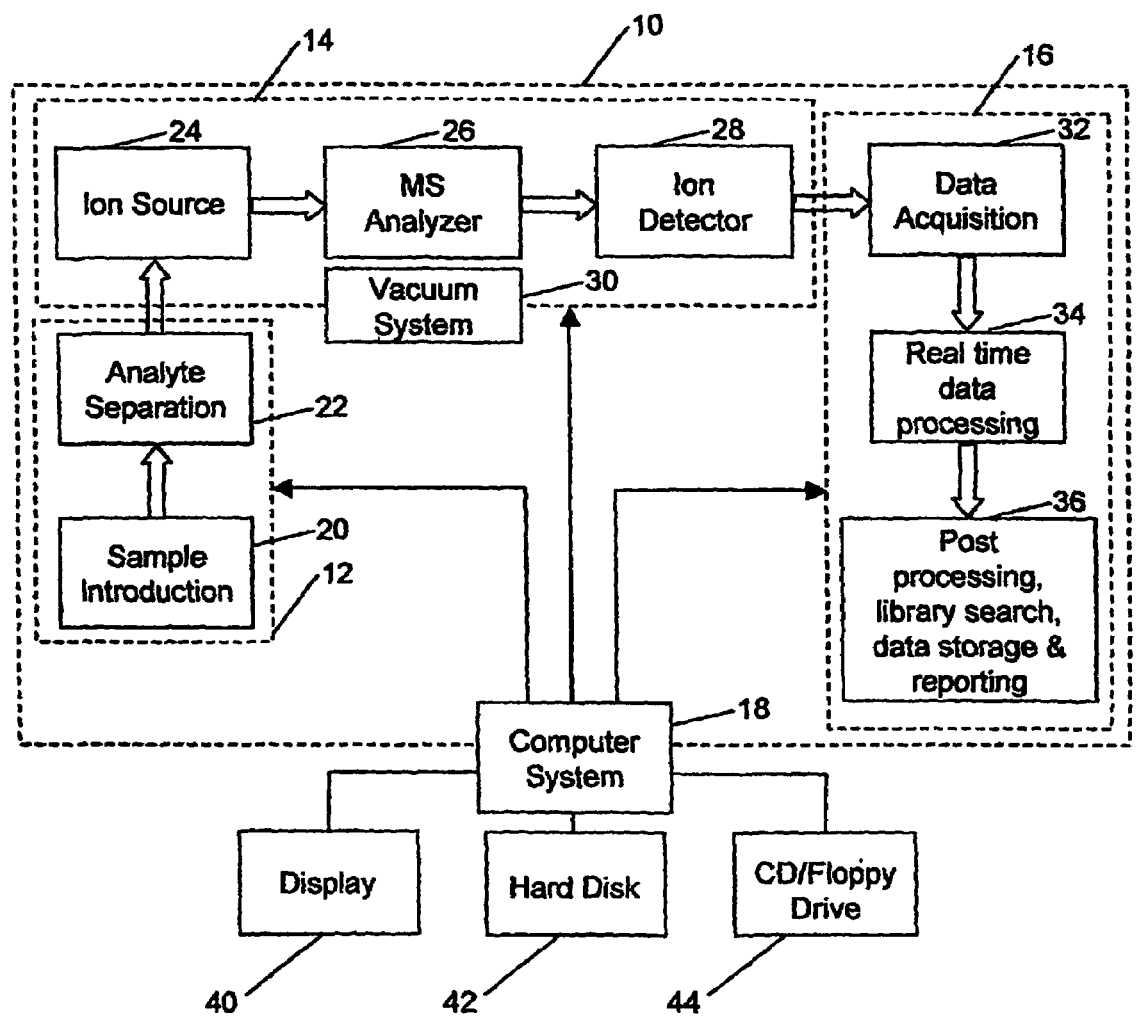
FIG. 1 is a block diagram of an analysis system in accordance with the invention, including a mass spectrometer.

Referring to FIG. 1, there is shown a block diagram of an analysis system 10, that may be used to analyze proteins or other molecules, as noted above, incorporating features of the present invention. Although the present invention will be described with reference to the single embodiment shown in the drawings, it should be understood that the present invention can be embodied in many alternate forms of embodiments. In addition, any suitable types of components could be used.

Analysis system 10 has a sample preparation portion 12, a mass spectrometer portion 14, a data analysis system 16, and a computer system 18. The sample preparation portion 12 may include a sample introduction unit 20, of the type that introduces a sample containing molecules of interest to system 10, such as Finnegan LCQ Deca XP Max, manufactured by Thermo Electron Corporation of Waltham, Mass., USA. The sample preparation portion 12 may also include an analyte separation unit 22, which is used to perform a preliminary separation of analytes, such as the proteins to be analyzed by system 10. Analyte separation unit 22 may be any one of a chromatography column, a gel separation unit, such as is manufactured by Bio-Rad Laboratories, Inc. of Hercules, Calif., and is well known in the art. In general, a voltage or PH gradient is applied to the gel to cause the molecules such as proteins to be separated as a function of one variable, such as migration speed through a capillary tube (molecular weight, MW) and isoelectric focusing point (Hannesh, S. M., *Electrophoresis* 21, 1202-1209 (2000)) for one dimensional separation or by more than one of these variables such as by isoelectric focusing and by MW (two dimensional separation). An example of the latter is known as SDS-PAGE.

The mass separation portion 14 may be a conventional mass spectrometer and may be any one available, but is preferably one of MALDI-TOF, quadrupole MS, ion trap MS, or FTICR-MS. If it has a MALDI or electrospray ionization ion source, such ion source may also provide for sample input to the mass spectrometer portion 14. In general, mass spectrometer portion 14 may include an ion source 24, a mass spectrum analyzer 26 for separating ions generated by ion source 24 by mass to charge ratio (or simply called mass), an ion detector portion 28 for detecting the ions from mass spectrum analyzer 26, and a vacuum system 30 for maintaining a sufficient vacuum for mass spectrometer portion 14 to operate efficiently. If mass spectrometer portion 14 is an ion mobility spectrometer, generally no vacuum system is needed.

The data analysis system 16 includes a data acquisition portion 32, which may include one or a series of analog to digital converters (not shown) for converting signals from ion detector portion 28 into digital data. This digital data is provided to a real time data processing portion 34, which process the digital data through operations such as summing and/or averaging. A post processing portion 36 may be used to do additional processing of the data from real time data processing portion 34, including library searches, data storage and data reporting.

Computer system 18 provides control of sample preparation portion 12, mass spectrometer portion 14, and data analysis system 16, in the manner described below. Computer system 18 may have a conventional computer monitor 40 to allow for the entry of data on appropriate screen displays, and for the display of the results of the analyses performed. Computer system 18 may be based on any appropriate personal computer, operating for example with a Windows® or UNIX® operating system, or any other appropriate operating system. Computer system 18 will typically have a hard drive 42, on which the operating system and the program for performing the data analysis described below is stored. A drive 44 for accepting a CD or floppy disk is used to load the program in accordance with the invention on to computer system 18. The program for controlling sample preparation portion 12 and mass spectrometer portion 14 will typically be downloaded as firmware for these portions of system 10. Data analysis system 16 may be a program written to implement the processing steps discussed below, in any of several programming languages such as C++, JAVA or Visual Basic.

Figure 2:
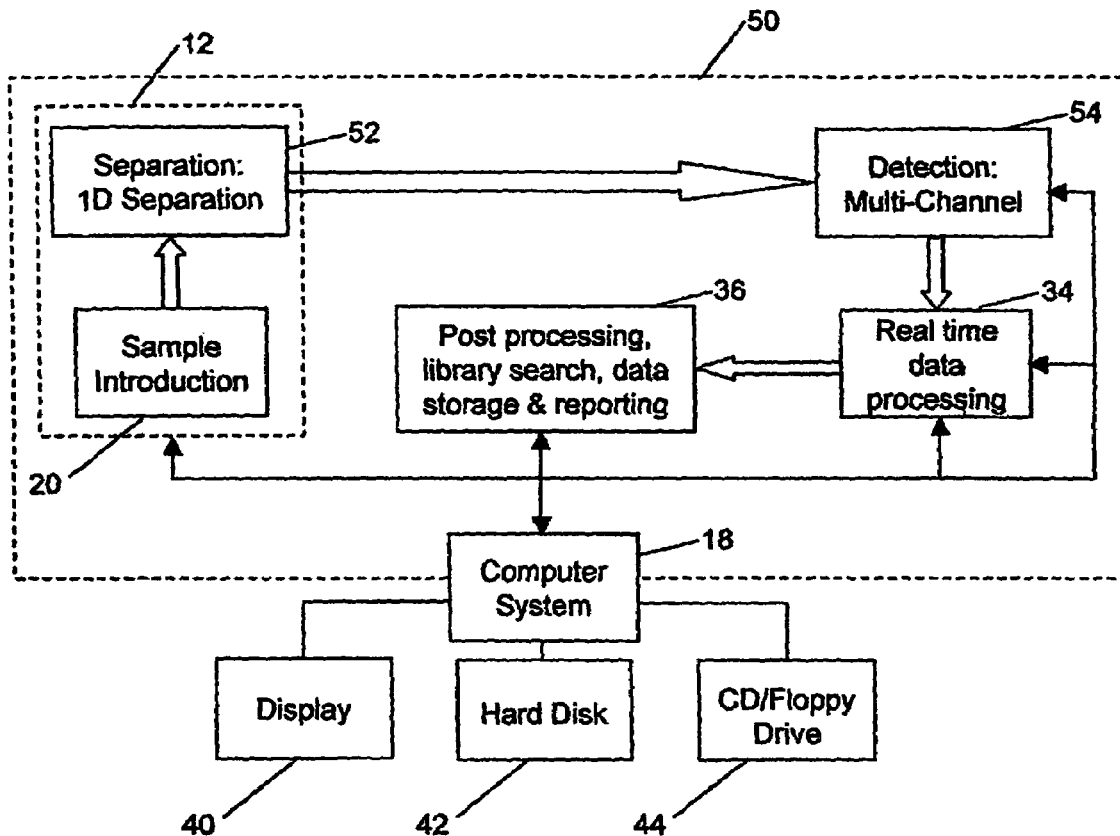
FIG. 2 is a block diagram of a system having one dimensional sample separation, and a multi-channel detector.

FIG. 2 is a block diagram of an analysis system 50 wherein the sample preparation portion 12 includes a sample introduction unit 20 and a one dimensional sample separation apparatus 52. By way of example, apparatus 52 may be a one dimensional electrophoresis apparatus. Separated sample components are analyzed by a multi-channel detection apparatus 54, such as, for example a series of ultraviolet sensors, or a mass spectrometer. The manner in which data analysis may be conducted is discussed below.

Figure 3:
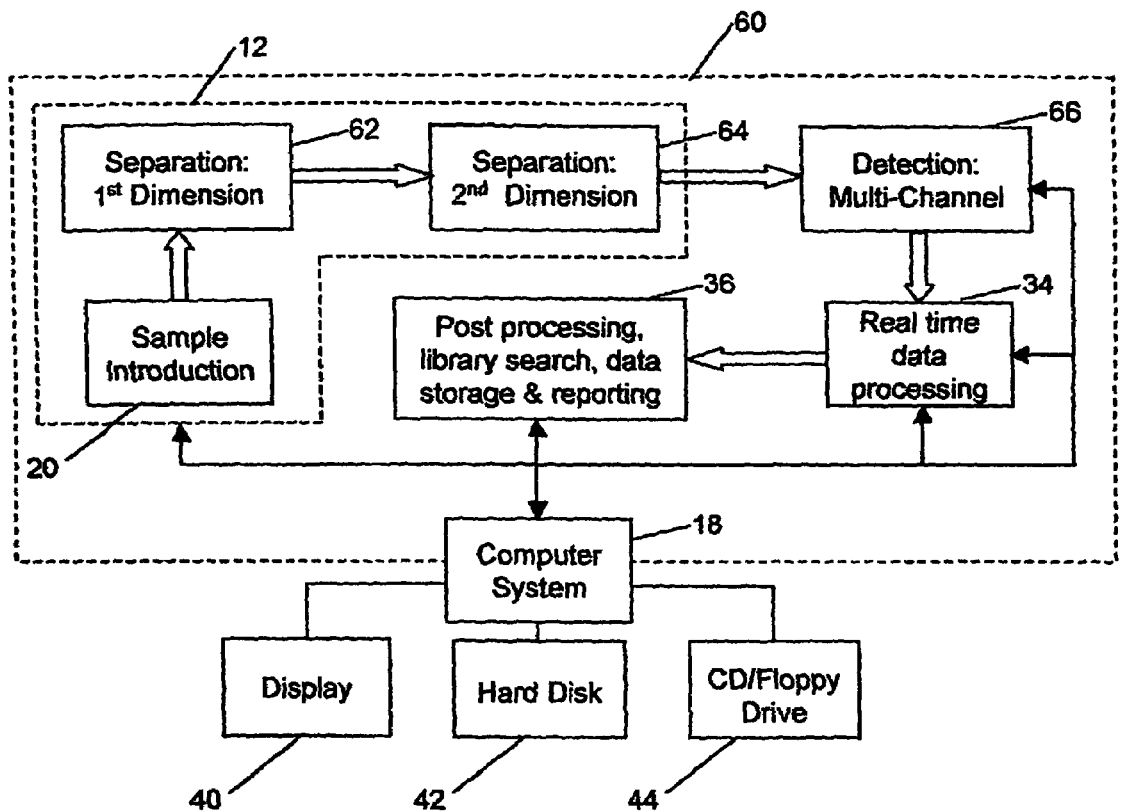
FIG. 3 is a block diagram of a system having two dimensional sample separation, and a single channel detector.

FIG. 3 is a block diagram of an analysis system 60, wherein the sample preparation portion 12 includes a sample introduction unit 20 and a first dimension sample separation apparatus 62 and a second dimension sample separation apparatus 64. By way of example, first dimension sample separation apparatus 62 and second dimension sample separation apparatus 64 may be two successive and different liquid chromatography units, or may be consolidated as a two-dimensional electrophoresis apparatus. Separated sample components are analyzed by a single channel detection apparatus 66, such as, for example a ultraviolet sensor with a 245 nm bandpass filter, or a gray scale gel imager. Again, the manner in which data analysis may be conducted is discussed below.

Figure 4A:
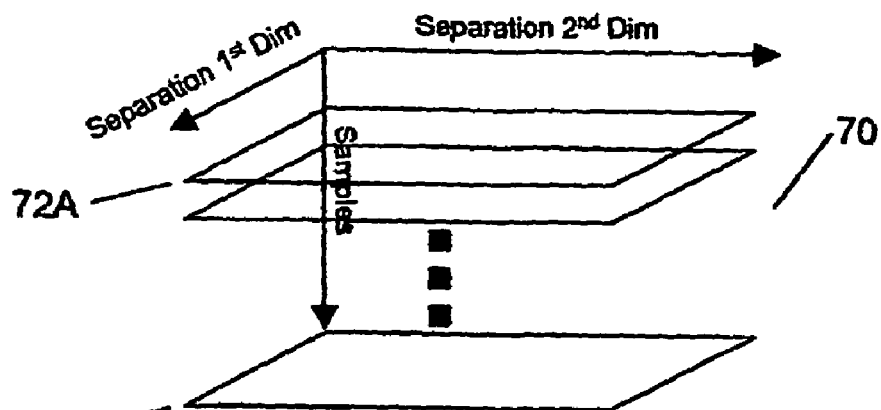
FIG. 4A, FIG. 4B and FIG. 4C illustrate the compilation of three-dimensional data arrays based on two-dimensional measurements, in accordance with the invention.

FIG. 4A illustrates a three-dimensional data array 70 compiled from a series of two-dimensional arrays 72A to 72N, representative of successive samples of a mixture of components to be analyzed. Two dimensional data arrays 72A to 72N may be produced by, for example, two dimensional gel electrophoresis, or successive chromatographic separations, as described above with respect to FIG. 3, or the combination of other separation techniques.

Figure 4B:
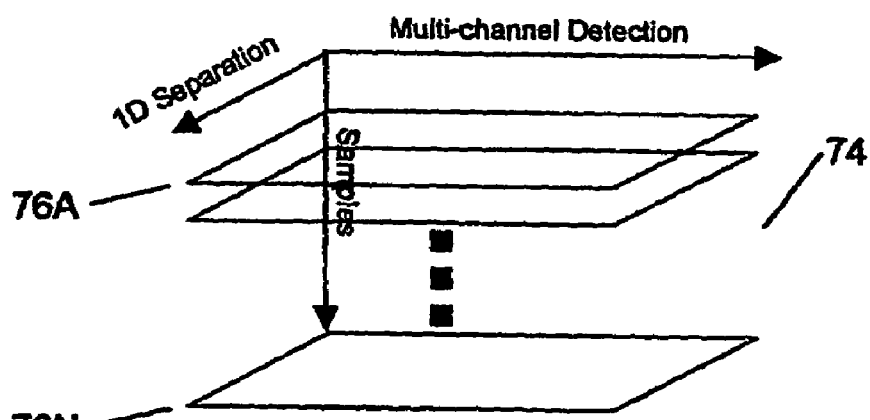

FIG. 4B illustrates a three-dimensional data array 74 compiled from a series of two-dimensional arrays 76A to 76N, representative of successive samples of a mixture of components to be analyzed. Two dimensional data arrays 72A to 72N may be produced by, for example, one dimensional gel electrophoresis, or liquid chromatography, followed by multi-channel analysis, as described above with respect to FIG. 2, or by other techniques such as gas chromatography/infrared spectroscopy (GC/IR) or LC/Fluorescence.

Figure 4C:
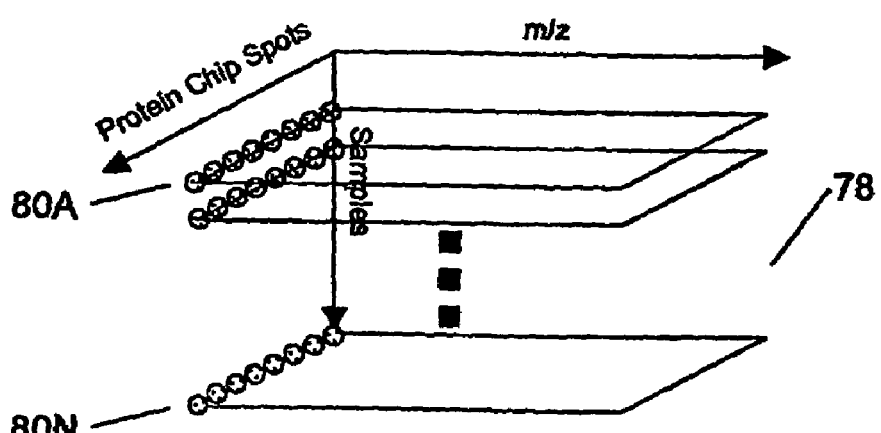

FIG. 4C illustrates a three-dimensional data array 78 compiled from a series of two-dimensional arrays 80A to 80N, representative of successive samples of a mixture of components to be analyzed. Two dimensional data arrays 72A to 72N are produced by, for example, protein affinity chips which are able to selectively bind proteins to defined regions (spots) on their surfaces of the type sold by Ciphergen Biosystems, Inc. of Fremont, Calif., USA, followed by multi-channel analysis, such as Surface Enhanced Laser Desorption/Ionization (SELDI) time of flight mass spectrometry, which may be one of the systems, as described above with respect to FIG. 2. Other techniques which may be used are 1D protein array combined with multi-channel fluorescence detection.

Figure 5:
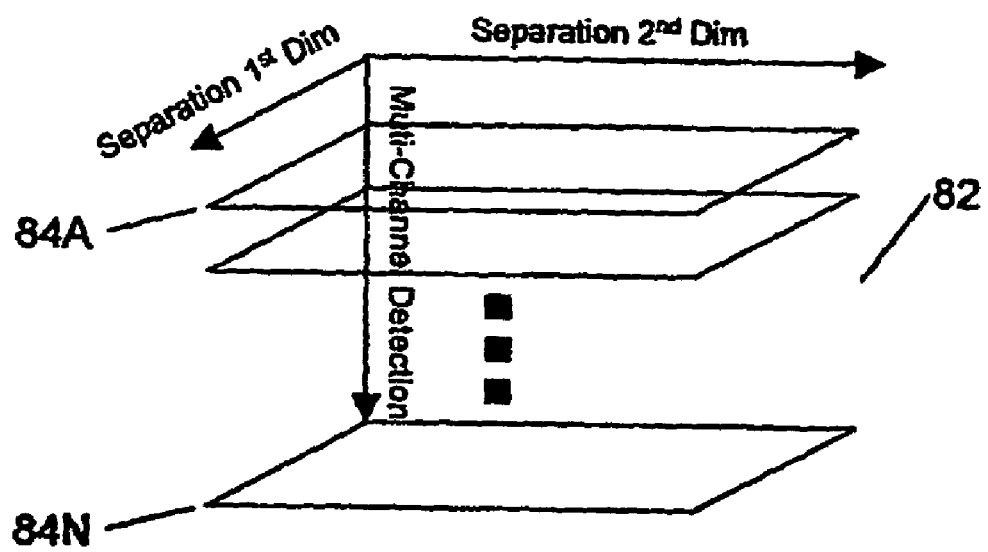
FIG. 5 illustrates a three dimensional data array based on single three-dimensional measurements with one sample.

FIG. 5 illustrates a three-dimensional data array 82 compiled from a series of two-dimensional arrays 84A to 84N, representative of a single sample of a mixture of components to be analyzed. Two dimensional data arrays 84A to 84N may be produced by, for example, two-dimensional gel electrophoresis, or successive liquid chromatography, as described above with respect to FIG. 1. Multi-channel detection by, for example mass spectrometry, as described above with respect to FIG. 1, that produces data in the third dimension. Other suitable techniques are 2D LC with multi-channel UV or fluorescence detection, 2D LC with IR detection, 2D protein array with mass spectrometry.

Figure 6:
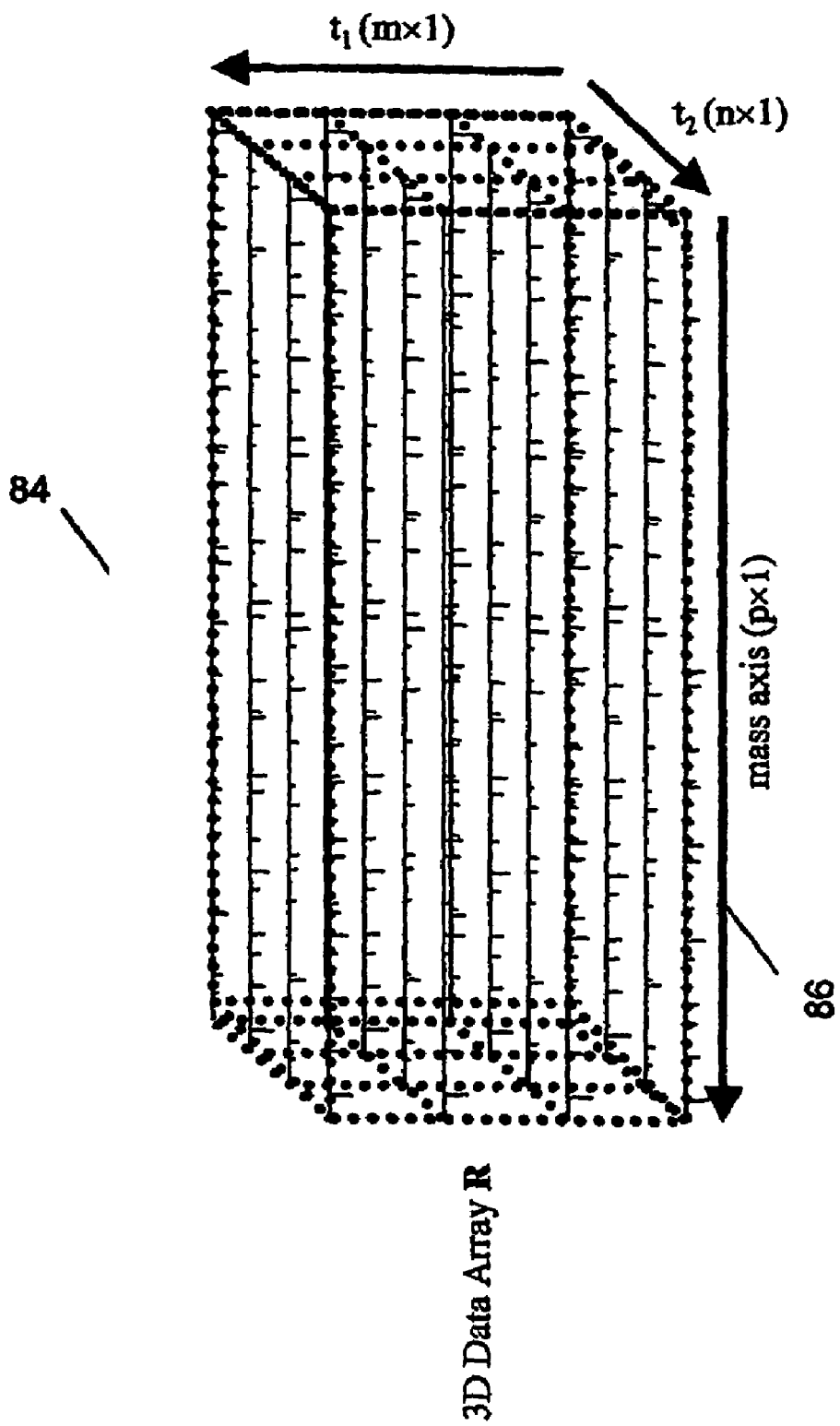
FIG. 6 illustrates a three-dimensional data array based on two-dimensional liquid phase separation followed by mass spectral detection.

FIG. 6 illustrates a data array 84 obtained by two-dimensional liquid phase separation (for example strong cation exchange chromatography followed by reversed phase chromatography). The third dimension is represented by the data along a mass axis 86 from mass spectral detection.

The data arrays of FIGS. 4A, 4B, 4C, 5 and 6 contain terms representative of all components in all of the samples or of a single, as the case may be (including the components of any calibration standards).

Figure 7:
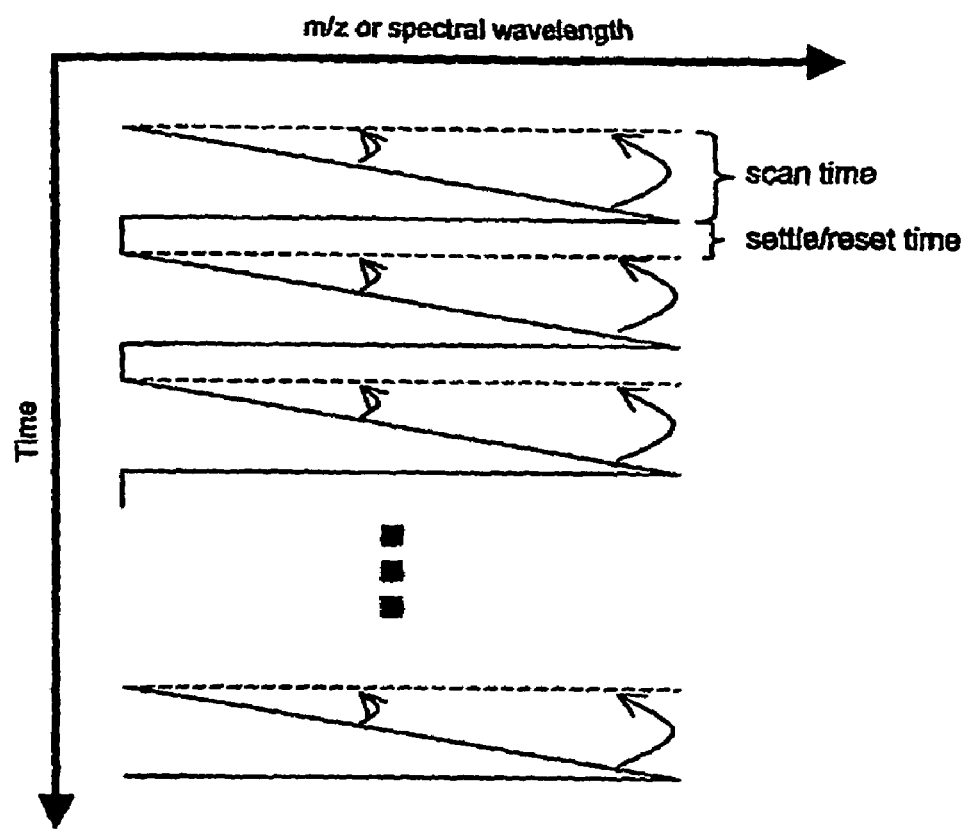
FIG. 7 illustrates time skew correction for multi-channel detection with sequential scanning.

FIG. 7 illustrates correction for time skew of the a scanning multi-channel detector connected to a time-based separation, as is the case in LC/MS where the LC is connected to a mass spectrometer which sweeps through a certain mass range during a predetermined scanning time. This type of time skew exists for most of mass spectrometers with the exception of simultaneous systems such as a magnetic sector system which detects ions of all masses simultaneously. Other examples include GC/IR where volatile compounds are separated in terms of retention time after passing through a column while IR spectrum is being acquired through either a scanning monochromator or an interferometer. When a time-dependent event such as a separation or reaction is connected to a detection system that sequentially scans through multiple channels, a time skew is generated where channels scanned earlier correspond to an earlier point in time for the event whereas the channels scanned later would correspond to a later point in time for the event. This time skew can be corrected by way of interpolation on a channel-by-channel basis to generate multi-channel data that correspond to the same point in time for all channels, i.e., to interpolate for each channel from the solid tilted lines onto the corresponding dashed horizontal lines in FIG. 7.

Figure 8:
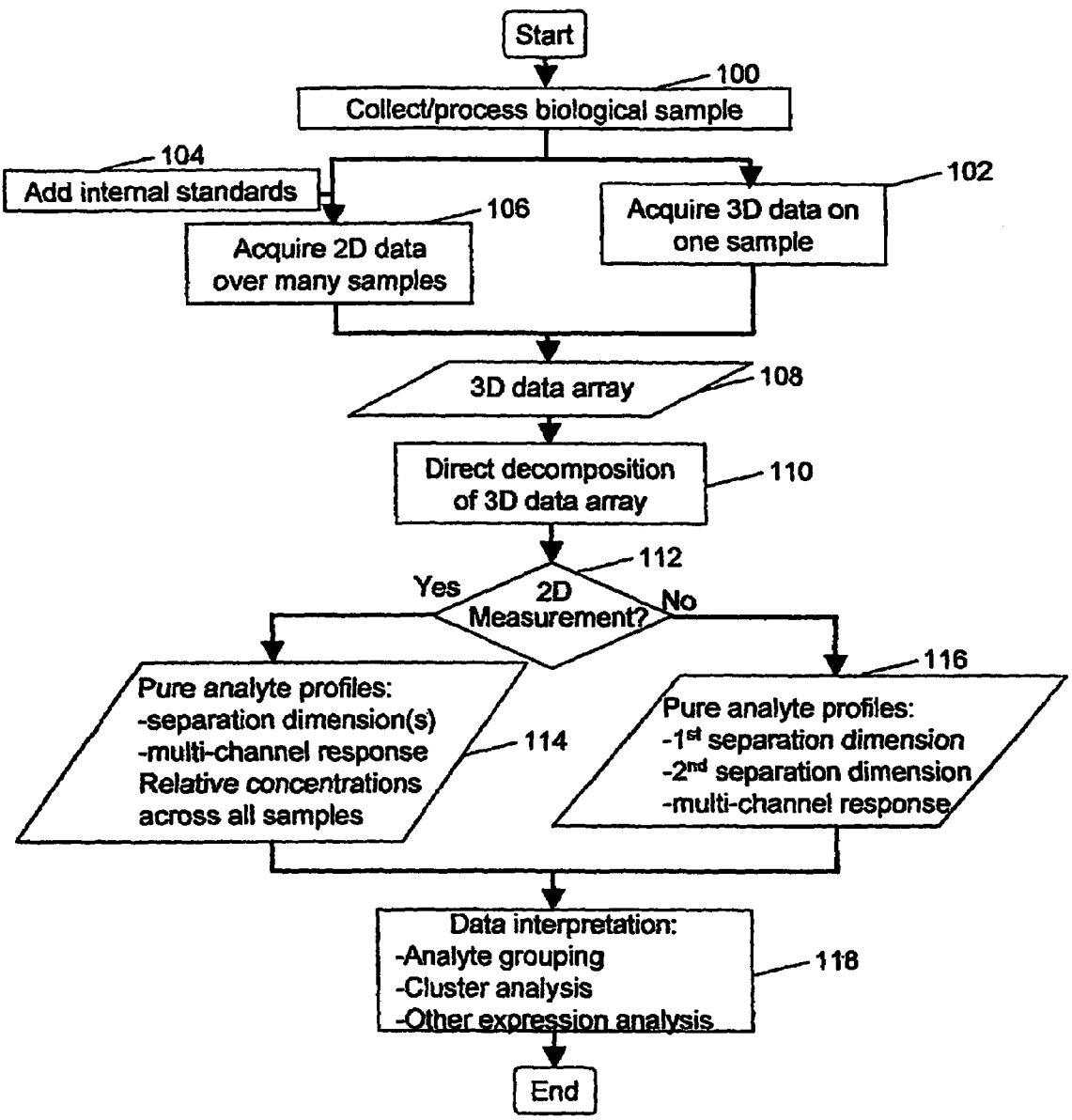
FIG. 8 is a flow chart of a method of analysis in accordance with the invention.
Figure 10:
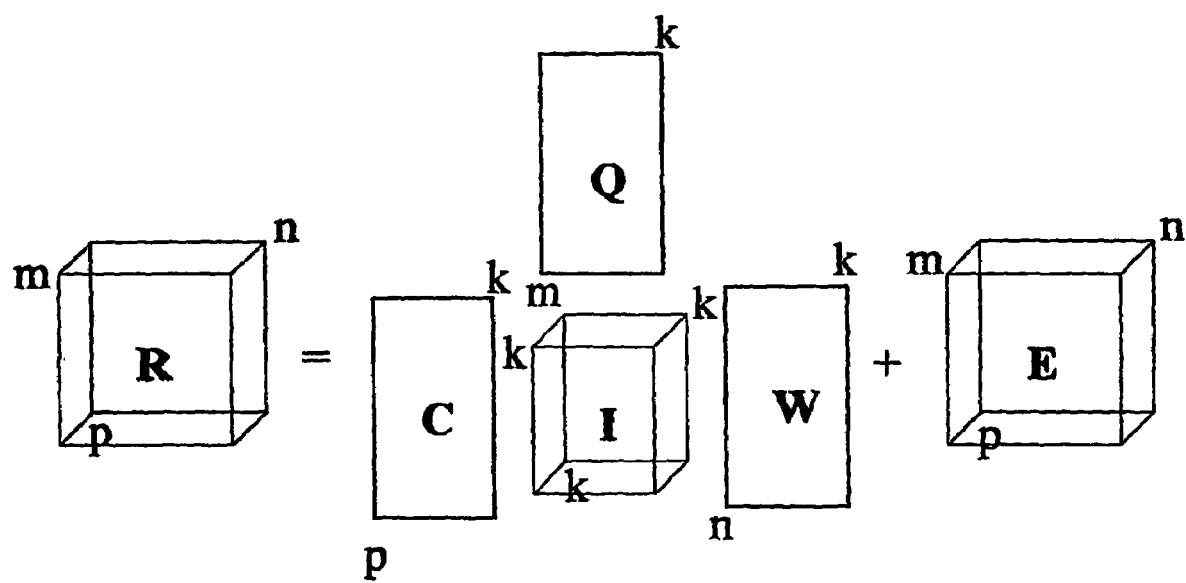
FIG. 10 illustrates direct decomposition of a three-dimensional data array.

FIG. 8 is a general flow chart of how sample data is acquired and processed in accordance with the invention.

Collection and processing of samples, such as biological samples, is performed at 100. If a single sample is being processed, three-dimensional data is acquired at 102. If two-dimensional data is to be acquired with multiple samples at 106, an internal standard is optionally added to the sample at 104. As described with respect to any of the techniques and systems above, a three-dimensional data array is formed at 108. The three-dimensional data array undergoes direct decomposition at 110. Different paths are selected at 112 based on whether or not a two-dimensional measurement has been made. If two-dimensional measurements have been made, pure analyte profiles in each dimension are obtained at 114 along with their relative concentrations across all samples. If three-dimensional measurements have been made on a single sample, pure analyte profiles for all analytes in the sample along all three dimensions are obtained at 116. In either case, data interpretation, including analyte grouping, cluster analysis and other types of expression and analysis are conducted at 118 and the results are reported out on display 40 of computer system 18, associated with a system of one of FIG. 1, 2 or 3.

The modes of analysis of the data are described below, with respect to specific examples, which are provided in order to facilitate understanding of, but not by way of limitation to, the scope of the invention.

If the response matrix, $R_j$ (m×n), for a typical sample can be expressed in the following bilinear form:

$$R_j = \sum_{i=1}^{k} c_i x_i y_i^T$$

where $c_i$ is the concentration of the ith analyte, $x_i$ (m×1) is the response of this analyte along the row axis (e.g., LC elution profile or chromatogram of this analyte in LC/MS), $y_i$ (n×1) is the response of this analyte along the column axis (e.g., MS spectrum of this analyte in LC/MS), and k is the number of analytes in the sample. When the response matrices of multiple samples (j=1, 2, ..., p) are compiled, a 3D data array R (m×n×p) can be formed.

Thus, at the end of a 2D gel run, a gray-scale image can be generated and represented in a 2D matrix $R_j$ (dimensioned m by n, corresponding to m different pI values digitized into rows and n different MW values digitized into columns, for sample j). This raw image data need to be calibrated in both pI and MW axes to yield a standardized image $\underline{R}_j$, $$\underline{R}_j = A_j \underline{R}_j B_j$$

where $A_j$ is a square matrix dimensioned as m by m with nonzero elements along and around the main diagonal (a banded diagonal matrix) and $B_j$ is another square matrix (n by n) with nonzero elements along and around the main diagonal (another banded diagonal matrix). The matrices $A_j$ and $B_j$ can be as simple as diagonal matrices (representing simple linear scaling) or as complex as increasing or decreasing bandwidths along the main diagonals (correcting for at least one of band shift, broadening, and distortion or other types of nonlinearity). A graphical representation of the above equation in its general form can be given as illustrated in FIG. 9:

$$\begin{bmatrix} \# & \cdots & \# \\ \cdot & & \cdot \\ \cdot & \cdots & \cdot \\ \cdot & & \cdot \\ \# & \cdots & \# \end{bmatrix} = \begin{bmatrix} \# & & & & \\ \# & \# & & & \\ & \# & \square & \# & \\ & & & \square & \# \\ & & & & \# & \# \end{bmatrix} \begin{bmatrix} \# & \cdots & \# \\ \cdot & & \cdot \\ \cdot & \cdots & \cdot \\ \cdot & & \cdot \\ \# & \cdots & \# \end{bmatrix} \begin{bmatrix} \# & \# & & & \\ \# & \# & & & \\ & \# & \square & & \\ & & \square & \# & \\ & & & \# & \# \end{bmatrix}$$

$$\underline{R}_j \qquad A_j \qquad \underline{R}_j \qquad B_j$$

When 2-D gel data from multiple samples are collected, a set of $\underline{R}_j$ can be arranged to form a 3D data array R as $$R = \begin{bmatrix} \underline{R}_1 \\ \cdot \\ \cdot \\ \cdot \\ \underline{R}_p \end{bmatrix}$$

where p is the number of biological samples and with R dimensioned as m by n by p. This data array (in the shape of a cube or rectangular solid) can be decomposed with trilinear decomposition method based on GRAM (Generalized Rank Annihilation Method, direct decomposition through matrix operations without iteration, Sanchez, E. et al, *J. Chemometrics* 4, 29 (1990)) or PARAFAC (PARAllel FACtor analysis, iterative decomposition with alternating least squares, Carroll, J. et al, *Psychometrika* 3, 45 (1980); Bezemer, E. et al, *Anal. Chem.* 73, 4403 (2001)) into four different arrays and a residual data array E:

[diagram: R = C · I · W + E cube decomposition]

where C represents the relative concentrations of all identifiable proteins (k of them with k≦min(m,n)) in all p samples, Q represents the pI profiles digitized at m pI values for each protein (k of them), W represents the molecular weight profiles digitized at n values for each protein (ideally a single peak will be observed that corresponds to each protein), and I is a new data cube with scalars on its super-diagonal as the only nonzero elements.

When all proteins are distinct (with differing pI values and differing MW) with expression levels varying in a linearly independent fashion from sample to sample, the following direct interpretations of the results can be expected:

1. The k value from the above decomposition automatically be equal to the number of proteins.
2. Values in each row of matrix C, after scaling with the super-diagonal elements in I, represent the relative concentrations of these proteins in a particular sample.
3. Each column in matrix Q represents the deconvolved pI profile of a particular protein.
4. Each column in matrix W represents the deconvolved MW profile of a particular protein.

If these proteins are distinct but with correlated expression levels from sample to sample (matrix C with linearly dependent columns), the interpretation can only be performed on the group of proteins having correlated expression levels, not on each individual proteins, a finding of significance for proteomics research.

Based on the decomposition presented above, the power of such multidimensional system and analysis can be immediately seen:

a. As a result of this decomposition that separates the composite responses into linear combinations of individual protein responses in each dimension, the quantitative information can be obtained for each protein in the presence of all other proteins.

b. The decomposition also separates out the profiles for each individual protein in each dimension, providing qualitative information for the identification of these proteins in both dimensions (pI and MW in 2DE and the chromatographic and the mass spectral dimension in LC/MS).

c. Each sample in the 3D data array R can contain a different set of proteins, implying that the proteins of interest can be identified and quantified in the presence of unknown proteins with only the common proteins shared by all samples in the data array have all nonzero concentrations in the decomposed matrix C.

d. A minimum of only two distinct samples will be required for this analysis, providing for a much better way to perform differential proteomic analysis without labels such as in ICAT to quickly and reliably pick out the proteins of interest in the presence of other un-interesting proteins.

e. The number of analytes that can be analyzed is limited by the maximum allowable pseudo-rank for each response matrix $R_j$, which can easily reach thousands (ion trap MS) to hundreds of thousands (TOF or FTICR-MS), paving the way for large scale proteomic analysis on complex biological samples.

f. A typical LC/MS run can be completed in less than 2 hours with no other chemical processes or sample preparation steps involved, pointing to at least 10-fold gain in throughput and tremendous simplification in informatics.

g. Since full LC/MS data are used in the analysis, nearly 100% sequence coverage can be achieved without the MS/MS experiments.

An important advantage of the above analysis, based on an image of the 2-D gel separation is that it is non-destructive and one can follow up with further confirmation through the use of, for example, MALDI TOF. The above analysis can also be applied to protein digests where all peptides from the same protein can be treated as a distinct group for analysis and interpretation. The separation of pI and MW profiles into individual proteins can still be performed when separation into individual peptides is not feasible.

Left and right transformation matrices $A_j$ and $B_j$ can be preferably determined using internal standards added to each sample. These internal standards are selected to cover all pI and MW ranges, for example, five internal standards with one on each corner of the 2D gel image and one right in the center. The concentrations of these internal standards would vary from one sample to another so that the corresponding matrix C in the above decomposition can be partitioned as $$C = [C_s | C_{unk}]$$

where all columns in $C_s$ are independent, i.e., $C_s$ is full rank, or better yet, the ratio between the largest and the smallest singular value is minimized. Now with part of the matrix C known in the above decomposition, it is possible to perform the decomposition such that the transformation matrices $A_j$ and $B_j$ for each sample (j=1, 2, . . . p) can be determined in the same decomposition process to minimize the overall residual E. The scale of the problem can be drastically reduced by parameterizing the nonzero diagonal bands in $A_j$ and $B_j$, for example, by specifying a band-broadening filter of Gaussian shape for each row in $A_j$ and each column in $B_j$ and allowing for smooth variation of the Gaussian parameters down the rows in $A_j$ and across the columns in $B_j$. With matrices $A_j$ and $B_j$ properly parameterized and analytical forms of derivatives with respect to the parameters derived, an efficient Gauss-Newton iteration approach can be applied to the trilinear decomposition or PARAFAC algorithm to arrive at both the desired decomposition and the proper transformation matrices $A_j$ and $B_j$ for each sample.

Compared with ICAT (isotope-coded affinity tags, Gygi, S. P. et al, *Nature Biotech.* 1999, 17, 994), this approach is not limited to analyzing only two samples and does not require peptide sequencing for protein identifications. The number of samples that can be quantified can be in the hundreds to thousands or even tens of thousands and the protein identification can be accomplished through the mass spectral data alone once all these proteins have been mathematically resolved and separated. Furthermore, there is no additional chemistry involving isotope labels, which should reduce the risk of losing many important proteins during the tedious sample preparation stages required for ICAT.

In brief, the present invention, using the method of analysis described above, provides a technique for protein identification and protein expression analysis using 2D data having the following features:

2D gel data from multiple samples is used to form a 3D data array;

for each of the following scenarios there will be a different set of interpretations applicable:

a) where all proteins are distinct with expression levels varying independently from sample to sample, b) where all proteins are distinct with correlated expression levels from sample to sample;

avoids centroiding on mass spectral continuum data;

raw mass spectral data alone can be directly utilized and is sufficient as inputs into the data array decomposition;

full mass spectral calibration, as for example that performed in U.S. patent application Ser. No. 10/689,313, may be optionally performed on the raw continuum data to obtain fully calibrated continuum data as inputs to the analysis, allowing for even more accurate mass determination and library search for the purpose of protein identification once deconvolved mass spectrum becomes available for an individual protein after the array decomposition.

this approach is based on mathematics instead of physical sequencing to resolve and separate proteins and does not require peptide sequencing for protein identifications, the results are both qualitative and quantitative, gel spot alignment and matching is automatically built into the data analysis.

Furthermore, it is preferred to have fully calibrated continuum mass spectral data in this invention to further improve mass alignment and spectral peak shape consistency, as described in co-pending application Ser. No. 10/689,313, a brief summary of which is set forth below.

Producing Fully Calibrated Continuum Mass Spectral Data

A calibration relationship of the form:

$$m = f(m_0) \quad \text{(Equation A)}$$

can be established through a least-squares polynomial fit between the centroids measured and the centroids calculated using all clearly identifiable isotope clusters available in the mass spectral standard across the mass range.

In addition to this simple mass calibration, additional full spectral calibration filters are calculated to serve two purposes simultaneously: the calibration of mass spectral peak shapes and mass spectral peak locations. Since the mass axis may have been pre-calibrated, the mass calibration part of the filter function is reduced in this case to achieve a further refinement on mass calibration, i.e., to account for any residual mass errors after the polynomial fit given by Equation A.

This total calibration process applies easily to quadrupole-type MS including ion traps where mass spectral peak width (Full Width at Half Maximum or FWHM) is generally roughly consistent within the operating mass range. For other types of mass spectrometer systems such as magnetic sectors, TOF, or FTMS, the mass spectral peak shape is expected to vary with mass in a relationship dictated by the operating principle and/or the particular instrument design. While the same mass-dependent calibration procedure is still applicable, one may prefer to perform the total calibration in a transformed data space consistent with a given relationship between the peak width/location and mass.

In the case of TOF, it is known that mass spectral peak width (FWHM) $\Delta m$ is related to the mass (m) in the following relationship:

$$\Delta m = a\sqrt{m}$$

where a is a known calibration coefficient. In other words, the peak width measured across the mass range would increase with the square root of the mass. With a square root transformation to convert the mass axis into a new function as follows:

$$m' = \sqrt{m}$$

where the peak width (FWHM) as measured in the transformed mass axis is given by $$\frac{\Delta m}{2\sqrt{m}} = \frac{a}{2}$$

which will remain unchanged throughout the spectral range.

For an FT MS instrument, on the other hand, the peak width (FWHM) $\Delta m$ will be directly proportional to the mass m, and therefore a logarithm transformation will be needed:

$$m' = \ln(m)$$

where the peak width (FWHM) as measured in the transformed log-space is given by $$\ln\left(\frac{m + \Delta m}{m}\right) = \ln\left(1 + \frac{\Delta m}{m}\right) \approx \frac{\Delta m}{m}$$

which will be fixed independent of the mass. Typically in FTMS, $\Delta m/m$ can be managed on the order of $10^{-5}$, i.e., $10^5$ in terms of the resolving power $m/\Delta m$.

For a magnetic sector instrument, depending on the specific design, the spectral peak width and the mass sampling interval usually follow a known mathematical relationship with mass, which may lend itself a particular form of transformation through which the expected mass spectral peak width would become independent of mass, much like the way the square root and logarithm transformation do for the TOF and FTMS.

When the expected mass spectral peak width becomes independent of the mass, due either to the appropriate transformation such as logarithmic transformation on FTMS and square root transformation on TOF-MS or the intrinsic nature of a particular instrument such as a well designed and properly tuned quadrupole or ion trap MS, huge savings in computational time will be achieved with a single calibration filter applicable to the full mass spectral range. This would also simplify the requirement on the mass spectral calibration standard: a single mass spectral peak would be required for the calibration with additional peak (s) (if present) serving as check or confirmation only, paving the way for complete mass spectral calibration of each and every MS based on an internal standard added to each sample to be measured.

There are usually two steps in achieving total mass spectral calibration. The first steps is to derive actual mass spectral peak shape functions and the second step is to convert the derive actual peak shape functions into a specified target peak shape functions centered at correct mass locations. An internal or external standard with its measured raw mass spectral continuum $y_0$ is related to the isotope distribution y of a standard ion or ion fragment by $$y_0 = y \otimes p$$

where p is the actual peak shape function to be calculated. This actual peak shape function is then converted to a specified target peak shape function t (a Gaussian of certain FWHM, for example) through one or more calibration filters given by $$t = p \otimes f$$

The calibration filters calculated above can be arranged into the following banded diagonal filter matrix:

$$F = \begin{bmatrix} f_1 & & & \\ & \cdots & & \\ & & f_i & \\ & & & \cdots \\ & & & & f_n \end{bmatrix}$$

in which each short column vector on the diagonal, $f_i$, is taken from the convolution filter calculated above for the corresponding center mass. The elements in $f_i$ is taken from the elements of the convolution filter in reverse order, i.e., $$f_i = \begin{bmatrix} f_{i,m} \\ f_{i,m-1} \\ \cdot \\ \cdot \\ \cdot \\ f_{i,1} \end{bmatrix}$$

As an example, this calibration matrix will have a dimension of 8,000 by 8,000 for a quadrupole MS with mass coverage up to 1,000 amu at ⅛ amu data spacing. Due to its sparse nature, however, typical storage requirement would only be around 40 by 8,000 with an effective filter length of 40 elements covering a 5-amu mass range.

Returning to the present invention, further multivariate statistical analysis can be applied to matrix C to study and understand the relationships between different samples and different proteins. The samples and proteins can be grouped or cluster-analyzed to see which proteins expressed more within what sample groups. For example, a dendrogram can be created using the scores or loadings from the principal component analysis of the C matrix. Typical conclusions include that cell samples from healthy individuals clustered around each other while those from diseased individuals would cluster around in a different group. For samples collected over a period of time after certain treatment, the samples may show a continuous change in the expression levels of some proteins, indicating a biological reaction to the treatment on the protein level. For samples collected over a series of dosages, the changes in relevant proteins can indicate the effects of dosages on this set of proteins and their potential regulations.

Figure 11:
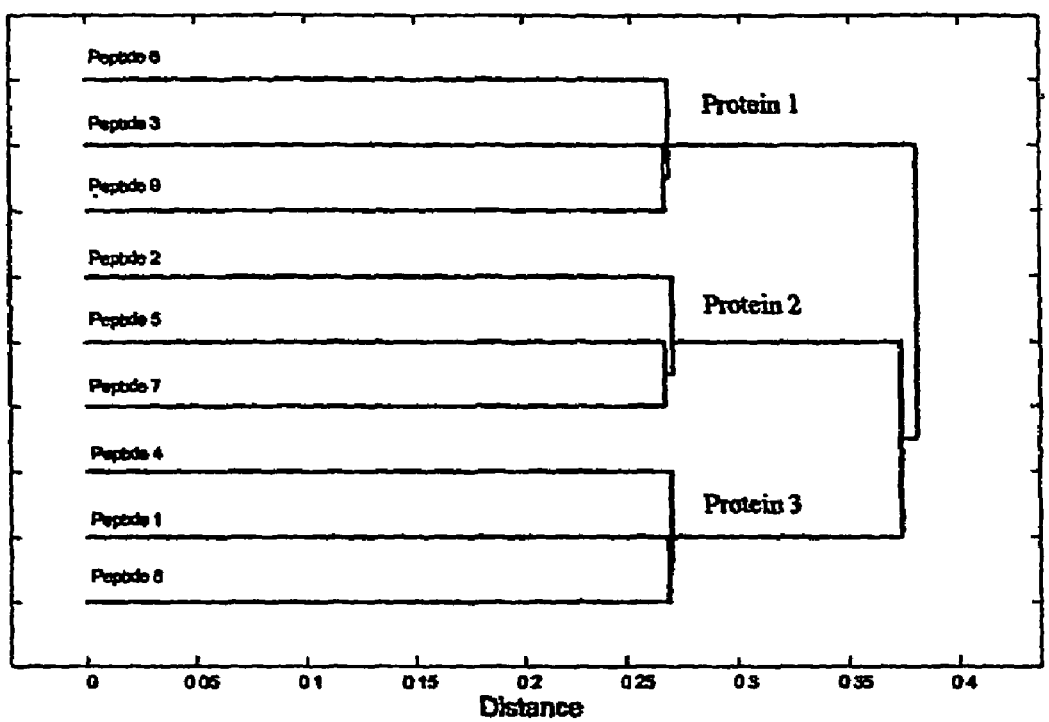
FIG. 11 illustrates grouping of peptides (a dendrogram) resulting from enzymatic digestion into proteins through cluster analysis, in accordance with the invention.

In the case where proteins are pre-digested into peptides before the analysis, each column in matrix C would represent a linear combination of a group of peptides coming from the same protein or a group of proteins showing similar expression patterns from sample to sample. A dendrogram performed to classify columns in matrix C, such as the one shown in FIG. 11, would group individual peptides back into their respective proteins and thus accomplish the analysis on the proteome level.

Qualitative (or signatory) information for the proteins identified can be found in pI profile matrix Q and MW matrix W. The qualitative information can serve the purpose of protein identification and even library searching, especially if the molecular weight information is determined with sufficient accuracy. In summary, the three matrices C, Q, and W when combined, allow for both protein quantification and identification with automatic gel matching and spot alignment from the determination of transformation matrices represented by $A_j$ and $B_j$.

The above 2-D data can come in different forms and shapes. An alternative to MALDI-TOF after excising/digesting 2-D gel spots is to run these samples through conventional LC/MS, for example on the Thermal Finnigan LCQ system, to further separate proteins from each gel spot before MS analysis. A very important application of this approach allows for rapid and direct protein identification and quantitation by avoiding 2-D gel (2DE) separation all together, thus increasing the throughput by orders of magnitude. This can be accomplished through the following steps:

1. Directly digest the sample containing hundreds and tens of thousands of proteins without any separation 2. Run the digested sample on a conventional LC/MS instrument to obtain a two-dimensional array. It should be noted that MS/MS capability is not a requirement in this case, although one may chose to run the sample on a LC/MS/MS system, which generates additional sequencing information.
3. Repeat 1 and 2 for multiple samples to generate a three-dimensional data array.
4. Decompose the data array using the approach outlined above.
5. Replace the pI axis with LC retention time and the MW axis with the mass axis in interpretation and mass spectral searching for the purpose of protein identification. The mathematically separated mass spectra can be further processed through centroiding and de-isotoping to yield stick spectra consistent with conventional databases and search engines such as Mascot or SwissProt, available online from: http://www.matrixscience.com or from http://us.expasy.org/sprot/. It is preferable, however, to fully calibrate the raw mass spectral continuum data into calibrated continuum data prior to the data array decomposition to yield fully calibrated continuum mass spectral data for each deconvolved protein or peptide. This continuum mass spectral data would then be used along with its high mass accuracy without centroiding for protein identification through a novel database search in a co-pending patent.

Depending on the nature of the LC column, the LC can act as another form of charge separation, similar to the pI axis in 2-D gel. The mass spectrometer in this case serves as a precise means for molecular weight measurement, similar to the WM axis in 2-D gel analysis. Due to the high mass accuracy available on a mass spectrometer, the transformation matrix $B_j$ can be reduced to a diagonal matrix to correct for mass-dependent ionization efficiency changes or even an identity matrix to be dropped out of the equation, especially after the full mass spectral calibration mentioned above. In order to handle large protein molecules, the protein sample is typically pre-digested into peptides through the use of enzymatic or chemical reactions, for example, tripsin. Therefore, it is typical to see multiple LC peaks as well as multiple masses for each protein of interest. While this may add complexities for sample handling, it largely enhances the selectivity of library search and protein identification. Multiple digestions may be used to further enhance the selectivity. Taking this to the extreme, each protein may be digested into peptides of varying lengths beforehand (Erdman degradation) to yield complete protein sequence information from matrix W. This is a new technique for protein sequencing based on mathematics rather than physical sequencing as an alternative to LC tandem mass spectrometry. In applications including MS, the approach does not require any data preprocessing on the continuum data from mass scans, such as centroiding and de-isotoping as are typically done in commercial instrumentation that are prone to many unsystematic errors. The raw counts data can be supplied and directly utilized as inputs into the data array decomposition.

Other 2-D data that can yield similar results with identical approaches includes but is not limited to the following examples that have 2-D separation with single point detection, or 1-D separation with multi-channel detection, or 2-D multi-channel detection:

1. Each 1-D or 2-D gel spot can be treated as an independent sample for the subsequent LC/MS analysis to generate one LC/MS 2-D data array for each spot and a data array containing all gel spots and their LC/MS data arrays. Due to the added resolving power gained from both gel and LC separation, more proteins can be more accurately identified.
2. Other types of 2-D separation, such as pI/hydrophobicity, MW/hydrophobicity, or a 1-D separation using either pI, MW, or hydrophobicity and a form of multi-channel electromagnetic or mass spectral detection, such as 1-D gel combined with on-the-gel MALDI TOF, or LC/TOF, LC/UV, LC/Fluorescence, etc. can be used.
3. Other types of 2-D separations such as 2-D liquid chromatography, with a single-channel detection (UV at 245 nm or fluorescence-tagged to be measured at one wavelength) can be used.
4. 1D or 2D protein arrays coupled with mass spectral or other multi-channel detection where each element on the array captures a particular combination of proteins in a way not dissimilar to LC columns can be used. These 1D or 2D spots can be arranged into one dimension of the 2-D array with the other dimension being mass spectrometry. These protein spots are similar to sensor arrays such as Surface Acoustic Wave Sensors (SAWs, coated with GC column materials to selectively bind to a certain class of compounds) or electronic noses such as conductive polymer arrays on which a binding event would generate a distinct electrical signal.
5. Multi-wavelength emission and excitation fluorescence (EEM) on single sample with different proteins tagged differentially or specific to a segment of the protein sequence can be used.

In second order proteomics analysis, the data array is formed by the 2D response matrices from multiple samples. Another effective way to create a data array is to include one more dimension in the measurement itself such that a data array can be generated from a single sample on what is called a third order instrument. One such instrument starting to receive wide attention in proteomics is LC/LC/MS, amenable to the same decomposition to yield mathematically separated elution profiles in both LC dimensions and MS spectral responses for each protein present in the sample.

Thus, while the two-dimensional approaches outlined above are major improvements in the art, a three-dimensional approach has the advantages of being much faster, more reproducible, and simplicity arising from the fact that the sample stays in the liquid phase throughout the entire process. However, since many proteins are too large for conventional mass spectrometers, and all proteins in the sample may be digested into peptide fragments before LC separation and mass spectral detection, the number of peptides and the complexity of the system increases by at least one order of magnitude. This results in what appears to be an insurmountable problem for data handling and data interpretation. In addition, available approaches stop short at only the level of qualitative protein identification for samples of very limited complexity such as yeast (Washburn, M. P. et al, *Nat. Biotechnol.* 19, 242-247 (2001)). The approach presented below achieves both identification and quantification of anywhere from hundreds and up to tens of thousands of proteins in a single two-dimensional liquid chromatography-mass spectrometry (LC/LC/MS or 2D-LC/MS) run.

By way of example, either size exclusion and reversed phase liquid chromatography (SEC-RPLC) or strong cation exchange and reversed phase liquid chromatography (SCX-RPLC) can be used for initial separation. This is followed by mass spectrometry detection (MS) in the form of either electro-spray ionization (ESI) mass spectrometry or time-of-flight mass spectrometry. The set of data generated are arranged into a three dimensional data array, R, that contains mass intensity (count) data at different combinations of retention times ($t_1$ and $t_2$, corresponding to the retention times in each LC dimension, for example, SEC and RPHL retention times, digitized at m and n different time points) and masses (digitized at p different values covering the mass range of interest). A graphical representation of this data array is provided in FIG. 6.

It is important to note that while the mass spectral data can be preprocessed into stick spectral form through centroiding and de-isotoping, it is not desired for this approach to work. Raw mass spectral continuum data can work better, due to the preservation of spectral peak shape information throughout the analysis and the elimination of all types of centroiding and de-isotoping errors mentioned above. A preferable approach is to fully calibration the continuum raw mass spectral data into calibrated continuum data to achieve high mass accuracy and allow for a more accurate library search.

At each retention time combination of $t_1$ and $t_2$ in data array R (dimensioned as m by n by p), the fraction of the sample injected into the mass spectrometer is composed of some linear combinations of a subset of the peptides in the original sample. This fraction of the sample is likely to contain somewhere between a few peptides to a few tens of thousands of peptides. The mass spectrum corresponding to such a sample fraction is likely to be very complex and, as noted above, the challenges of resolving such a mix into individual proteins for protein identification and especially quantification would seem to be insurmountable.

However, the three-dimensional data array, as noted above with respect to two-dimensional analysis, can be decomposed with trilinear decomposition method based on GRAM (Generalized Rank Annihilation Method, direct decomposition through matrix operation without iteration) or PARAFAC (PARAllel FACtor analysis, iterative decomposition with alternating least squares) into four different matrices and a residual data cube E as noted above.

In this three-dimensional analysis C represents the chromatograms with respect to $t_1$ of all identifiable peptides (k of them with $k \leq \min(m,n)$), Q represents the chromatograms with respect to $t_2$ of all identifiable peptides (k of them), W represents the deconvolved continuum mass spectra of all peptides (k of them), and I is a new data array with scalars on its super-diagonal as the only nonzero elements. In other words, through the decomposition of this data array, the two retention times ($t_1$ and $t_2$) have been identified for each and every peptide existing in the sample, along with precise determination of the mass spectral continuum for each peptide contained in W.

The foregoing analysis yield information on the peptide level, unless intact proteins are directly analyzed without digestion and with a mass spectrometer capable of handling larger masses. The protein level information, however, can be obtained from multiple samples through the following additional steps may be taken:

1. Perform the 2D-LC/MS runs as described above for multiple samples (1 of them) collected over a period of time with the same treatment, or at a fixed time with different dosages of treatment, or from multiple individuals at different disease states.
2. Perform the data decomposition for each sample as described above and fully identify all the peptides with each sample.
3. The relative concentrations of all peptides in each sample can be read directly from the super-diagonal elements in I. A new matrix S composed of these concentrations across all samples can be formed with dimensions of 1 samples by q distinct peptides in all samples ($q \square \max(k_1, k_2, \ldots, k_p)$ where $k_i$ is the number of peptides in sample i (i=1, 2, ..., p)). For samples that do not contain some of the peptides existing in other samples, the entries in the corresponding rows for these peptides (arranged in columns) would be zeros.
4. A statistical study of the matrix S will allow for examination of the peptides that change in proportion to each other from one sample to another. These peptides could potentially correspond to all the peptides coming from the same protein. A dendrogram based on Mahalanobis distance calculated from singular value decomposition (SVD) or principal component analysis (PCA) of the S matrix can indicate the inter-connectedness of these peptides. It should be pointed out, however, that there would be groups of proteins that vary in tandem from one sample to another and thus all their corresponding peptides would be grouped into the same cluster. A graphical representation of this process is provided in FIG. 11.
5. The matrix S so partitioned according to the grouping above represents the results of differential proteomics analysis showing the different protein expression levels across many samples.
6. For all peptides in each group identified in step 6 immediately above, the resolved mass spectral responses contained in W are combined to form a composite mass spectral signature of all peptides contained in each protein or group of proteins that change in tandem in their expression levels. Such composite mass spectrum can be either further processed into stick/centroid spectrum (if has not so processed already) or preferably searched directly against standard protein databases such as Mascot and SwissProt for protein identification using continuum mass spectral data as disclosed in the co-pending application.

Comparing to ICAT (Gygi, S. P. et al, *Nat. Biotechnol.* 17, 994-999 (1999)), the quantitation proposed here does not require any additional sample preparation, has the potential of handling many thousands of samples, and uses all available peptides (instead of a few available for isotope-tagging) in an overall least squares fit to arrive at relative protein expression levels. Due also to the mathematical isolation of all peptides and the later grouping back into proteins, the protein identification can be accomplished without peptide sequencing as is the case for ICAT. In the case of intact protein 2D-LC/MS analysis, all protein concentrations can be directly read off the super-diagonal in I, without any further re-grouping. It may however still to desirable to form the S matrix as above and perform statistical analysis on the matrix for the purpose of differential proteomics or protein expression analysis.

In brief, the present invention provides a method for protein identification and protein expression analysis using three dimensional data having the following features:

the set of data generated from either of the following methodologies is arranged into a 3D data array:
- a) size exclusion and reversed phase liquid chromatography (SEC-RPLC), or
- b) strong cation exchange and reversed phase liquid chromatography (SCX-RPLC), coupled with either:
  - i) electro-spray ionization (ESI) mass spectrometry for peptides after protein digestion, or
  - ii) time-of-flight (TOF) mass spectrometry for peptides or intact proteins;

here, the mass spectral data does not have to be preprocessed through centroiding and/or de-isotoping, though it is preferred to fully calibrate the raw mass spectral continuum;

mass spectral continuum data can be used directly and is in fact preferred, thus preserving spectral peak shape information throughout the analysis;

this approach is a method of mathematical isolation of all peptides and then later grouping back into proteins, thus the protein identification can be done without peptide sequencing;

the present invention provides a quantitative tool that does not require any additional sample preparation, has the potential of handling many thousands of samples, and uses all available peptides in an overall least squares fit to arrive at relative protein expression levels.

The above 3-D data can come in different forms and shapes. An alternative to 2D-LC/MS is to perform 2D electrophoresis separation coupled with electrospray ionization (ESI) mass spectrometry (conventional ion-trap or quadrupole-MS or TOF-MS). The analytical approach and process is identical to those described above. Other types of 3D data amenable to this approach include but are not limited to:

2D-LC with other multi-channel spectral detection by UV, fluorescence (with sequence-specific tags or tags whose fluorescence is affected by a segment of the protein sequence), etc.

3D electrophoresis or 3D LC with a single channel detection (UV at 245 nm, for example). The 3D separation can be applied to intact proteins to separate, for example, in pI, MW, and hydrophobicity.

1D electrophoresis followed by 1D-LC/MS on either digested or intact proteins.

2D gel separation followed by MS multi-channel detection. If digestion is needed, it can be accomplished on the gel with the proper MALDI matrix for on the gel TOF analysis.

Other 2D means of separation coupled with multi-channel detection.

1D separation coupled with 2D spectral detection, LC/MS/MS.

1D LC or 1D gel electrophoresis coupled with 2D spectral detection, for example, excitation-emission 2D fluorescence (EEM).

The methods of analysis of the present invention can be realized in hardware, software, or a combination of hardware and software. Any kind of computer system—or other apparatus adapted for carrying out the methods and/or functions described herein—is suitable. A typical combination of hardware and software could be a general purpose computer system with a computer program that, when being loaded and executed, controls the computer system, which in turn control an analysis system, such that the system carries out the methods described herein. The present invention can also be embedded in a computer program product, which comprises all the features enabling the implementation of the methods described herein, and which—when loaded in a computer system (which in turn control an analysis system), is able to carry out these methods.

Computer program means or computer program in the present context include any expression, in any language, code or notation, of a set of instructions intended to cause a system having an information processing capability to perform a particular function either directly or after conversion to another language, code or notation, and/or reproduction in a different material form.

Thus the invention includes an article of manufacture which comprises a computer usable medium having computer readable program code means embodied therein for causing a function described above. The computer readable program code means in the article of manufacture comprises computer readable program code means for causing a computer to effect the steps of a method of this invention. Similarly, the present invention may be implemented as a computer program product comprising a computer usable medium having computer readable program code means embodied therein for causing a function described above. The computer readable program code means in the computer program product comprising computer readable program code means for causing a computer to effect one or more functions of this invention. Furthermore, the present invention may be implemented as a program storage device readable by machine, tangibly embodying a program of instructions executable by the machine to perform method steps for causing one or more functions of this invention.

It is noted that the foregoing has outlined some of the more pertinent objects and embodiments of the present invention. The concepts of this invention may be used for many applications. Thus, although the description is made for particular arrangements and methods, the intent and concept of the invention is suitable and applicable to other arrangements and applications. It will be clear to those skilled in the art that other modifications to the disclosed embodiments can be effected without departing from the spirit and scope of the invention. The described embodiments ought to be construed to be merely illustrative of some of the more prominent features and applications of the invention. Thus, it should be understood that the foregoing description is only illustrative of the invention. Various alternatives and modifications can be devised by those skilled in the art without departing from the invention. Other beneficial results can be realized by applying the disclosed invention in a different manner or modifying the invention in ways known to those familiar with the art. Thus, it should be understood that the embodiments has been provided as an example and not as a limitation. Accordingly, the present invention is intended to embrace all alternatives, modifications and variances which fall within the scope of the appended claims.

What is claimed is:

1. A method for analyzing data obtained from at least one sample in a measurement system that has a capability for measuring components of a sample containing more than one component as a function of at least two different variables, said method comprising:
    obtaining data representative of at least one sample from said system, said data being expressed as a function of said at least two variables;
    forming a data stack having successive levels, each level containing one of said data samples;
    forming a data array representative of a compilation of all of the data in said data stack; and
    separating said data array into a series of matrixes in one overall decomposition process, said matrixes including:
        a concentration matrix representative of concentration of each component in said levels of data;
        a first profile of the components as a function of said first variable; and
        a second profile of the components as a function of said second variable; and
        at least one standardization matrix serving to calibrate one of said concentration or profile matrixes.

2. The method of claim 1, wherein said first profile and said second profile are representative of profiles of substantially pure components.

3. The method of claim 1, further comprising performing qualitative analysis using at least one of said first profile and said second profile.

4. The method of claim 1, further comprising standardizing data representative of said at least one sample by performing a data matrix multiplication of such data into the product of a first standardization matrix, the data itself, and a second standardization matrix, to form a standardized data matrix.

5. The method of claim 4, wherein terms in said first standardization matrix and said second standardization matrix have values that cause said data to be represented at positions with respect to said two variables, which are different in said standardized data matrix from those in said data array.

6. The method of claim 5, wherein said first standardization matrix shifts said data with respect to said first variable, and said second standardization matrix shifts said data with respect to said second variable.

7. The method of claim 5, wherein terms in said first standardization matrix and said second standardization matrix have values that serve to standardize distribution shapes of the data with respect to said first and second variable, respectively.

8. The method of claim 4, wherein terms in said first standardization matrix and said second standardization matrix are determined by:
applying a sample having known components to said apparatus; and
selecting terms for said first standardization matrix and said second standardization matrix which cause data produced by said known components to be positioned properly with respect to said first variable and said second variable.

9. The method of claim 8, wherein said terms are determined by selecting terms which produce a smallest error in position of said data with respect to said first variable and said second variable in said standardized data matrix.

10. The method of claim 9, wherein the terms of said first standardization matrix and said second standardization matrix are computed for each sample.

11. The method of claim 10, wherein terms of said first standardization matrix and said second standardization matrix are computed so as to produce a smallest error over all samples.

12. The method of claim 8, wherein values of terms in said first standardization matrix and said second standardization matrix are determined by solving said data array R:

$$R_{(m \times n \times p)} = C_{(p \times k)} \cdot I \cdot Q_{(m \times k)} \cdot W_{(n \times k)} + E_{(m \times n \times p)}$$

where Q (m×k) contains pure profiles of all k components with respect to the first variable, W (n×k) contains pure profiles with respect to the second variable for the components, C (p×k) contains concentrations of these components in all p samples, I is a new data array with scalars on its superdiagonal as the only nonzero elements, and E (m×n×p) is a residual data array.

13. The method of claim 4, wherein at least one of the first and second standardization matrices can be simplified to be either a diagonal matrix or an identity matrix.

14. The method of claim 4, wherein the terms in said first standardization matrix and said second standardization matrix are based on parameterized known functional dependence of said terms on said variables.

15. The method of claim 1, wherein said apparatus is a two-dimensional electrophoresis separation system.

16. The method of claim 15, wherein said first variable is isoelectric point and said second variable is molecular weight.

17. The method of claim 1, wherein said variables are a result of any combination, in no particular sequence, and including self-combination, of chromatographic separation, capillary electrophoresis separation, gel-based separation, affinity separation and antibody separation.

18. The method of claim 1, wherein one of the two variables is mass associated with the mass axis of a mass spectrometer.

19. The method of claim 18, wherein said apparatus further comprises a chromatography system for providing said samples to said mass spectrometer, retention time being another of the two variables.

20. The method of claim 18, wherein said apparatus further comprises an electrophoresis separation system for providing said samples to said mass spectrometer, migration characteristics of said sample being another of the two variables.

21. The method of claim 18, wherein said data is continuum mass spectral data.

22. The method of claim 18, wherein said data is used without centroiding.

23. The method of claim 18, further comprising correcting said data for time skew.

24. The method of claim 18, further comprising performing a calibration of said data with respect to mass and mass spectral peak shapes.

25. The method of claim 18, wherein the other one of said first variable and said second variable is that of a region on a protein chip having a plurality of protein affinity regions.

26. The method of claim 1, further comprising:
obtaining data for said data array by using a single channel analyzer and by analyzing the samples successively.

27. The method of claim 26, wherein said single channel detector is based on one of light absorption, light emission, light reflection, light transmission, light scattering, refractive index, electrochemistry, conductivity, radioactivity, or any combination thereof.

28. The method of claim 27, wherein the components in said sample are bound to at least one of fluorescence tags, isotope tags, stains, affinity tags, or antibody tags.

29. A computer readable medium comprising computer readable code thereon for causing a computer to analyze data by performing the method of one of claims 1-28.

30. A chemical analysis system configured to perform the method of one of claims 1-28.

31. The method of claim 1 wherein said at least one standardization matrix includes a first standardization matrix for shifting said data with respect to a first variable, and a second standardization matrix for shifting said data with respect to a second variable.

32. A method for analyzing data obtained from multiple samples in a separation system that has a capability for separating components of a sample containing more than one component as a function of two different variables, said method comprising:
obtaining data representative of multiple samples from said system, said data being expressed as a function of said two variables;
forming a data stack having successive levels, each level containing one of said data samples;
forming a data array representative of a compilation of all of the data in said data stack; and separating said data array into a series of matrixes, said matrixes being:
- a concentration matrix representative of concentration of each component in said sample;
- a first profile of the components as a function of said first variable;
- a second profile of the components as a function of said second variable; and
- a first standardization matrix and a second standardization matrix;

wherein said first standardization matrix shifts said data with respect to said first variable, and said second standardization matrix shifts said data with respect to said second variable.

33. The method of claim 32, wherein said at least one sample comprises a single sample, and said successive data is representative of said sample as a function of time.

34. The method of claim 32, wherein said at least one sample comprises a single sample, and said successive data is representative of said sample as a function of mass of its components.

35. The method of claim 34, wherein said at least one sample comprises a plurality of samples, and said successive data is representative of successive samples.

36. A method for analyzing data obtained from multiple samples in a separation system that has a capability for separating components of a sample containing more than one component as a function of two different variables, said method comprising:
- obtaining data representative of multiple samples from said system, said data being expressed as a function of said two variables;
- forming a data stack having successive levels, each level containing one of said data samples;
- forming a data array representative of a compilation of all of the data in said data stack;
- separating said data array into a series of matrixes, said matrixes being:
  - a concentration matrix representative of concentration of each component in said sample;
  - a first profile of the components as a function of said first variable; and
  - a second profile of the components as a function of said second variable; and
- standardizing data representative of a sample by performing a data matrix multiplication of such data into the product of a first standardization matrix, the data itself, and a second standardization matrix, to form a standardized data matrix;
- wherein terms in said first standardization matrix and said second standardization matrix have values that cause said data to be represented at positions with respect to said two variables, which are different in said standardized data matrix from those in said data array; and
- said first standardization matrix shifts said data with respect to said first variable, and said second standardization matrix shifts said data with respect to said second variable.

37. A method for analyzing data obtained from multiple samples in a separation system that has a capability for separating components of a sample containing more than one component as a function of two different variables, said method comprising:
- obtaining data representative of multiple samples from said system, said data being expressed as a function of said two variables;
- forming a data stack having successive levels, each level containing one of said data samples;
- forming a data array representative of a compilation of all of the data in said data stack;
- separating said data array into a series of matrixes, said matrixes being:
  - a concentration matrix representative of concentration of each component in said sample;
  - a first profile of the components as a function of said first variable; and
  - a second profile of the components as a function of said second variable; and
- standardizing data representative of a sample by performing a data matrix multiplication of such data into the product of a first standardization matrix, the data itself, and a second standardization matrix, to form a standardized data matrix;
- wherein terms in said first standardization matrix and said second standardization matrix have values that cause said data to be represented at positions with respect to said two variables, which are different in said standardized data matrix from those in said data array; and
- terms in said first standardization matrix and said second standardization matrix have values that serve to standardize distribution shapes of the data with respect to said first and second variable, respectively.

38. A method for analyzing data obtained from multiple samples in a separation system that has a capability for separating components of a sample containing more than one component as a function of two different variables, said method comprising:
- obtaining data representative of multiple samples from said system, said data being expressed as a function of said two variables;
- forming a data stack having successive levels, each level containing one of said data samples;
- forming a data array representative of a compilation of all of the data in said data stack;
- separating said data array into a series of matrixes, said matrixes being:
  - a concentration matrix representative of concentration of each component in said sample;
  - a first profile of the components as a function of said first variable; and
  - a second profile of the components as a function of said second variable; and
- standardizing data representative of a sample by performing a data matrix multiplication of such data into the product of a first standardization matrix, the data itself, and a second standardization matrix, to form a standardized data matrix;
- wherein terms in said first standardization matrix and said second standardization matrix are determined by:
- applying a sample having known components to said apparatus; and
- selecting terms for said first standardization matrix and said second standardization matrix which cause data produced by said known components to be positioned properly with respect to said first variable and said second variable; and which produce a smallest error in position of said data with respect to said first variable and said second variable in said standardized data matrix.

39. A method for analyzing data obtained from multiple samples in a separation system that has a capability for separating components of a sample containing more than one component as a function of two different variables, said method comprising:

obtaining data representative of multiple samples from said system, said data being expressed as a function of said two variables;

forming a data stack having successive levels, each level containing one of said data samples;

forming a data array representative of a compilation of all of the data in said data stack; and separating said data array into a series of matrixes, said matrixes being:

a concentration matrix representative of concentration of each component in said sample;

a first profile of the components as a function of said first variable; and a second profile of the components as a function of said second variable;

wherein said system is a two-dimensional electrophoresis separation system; said first variable is isoelectric point and said second variable is molecular weight.

40. A method for analyzing data obtained from multiple samples in a separation system that has a capability for separating components of a sample containing more than one component as a function of two different variables, said method comprising:

obtaining data representative of multiple samples from said system, said data being expressed as a function of said two variables;

forming a data stack having successive levels, each level containing one of said data samples;

forming a data array representative of a compilation of all of the data in said data stack; and separating said data array into a series of matrixes, said matrixes being:

a concentration matrix representative of concentration of each component in said sample;

a first profile of the components as a function of said first variable; and a second profile of the components as a function of said second variable;

wherein one of said first variables and said second variable is mass associated with the mass axis of a mass spectrometer; and another one of said first variable and said second variable is that of a region on a protein chip having a plurality of protein affinity regions.

\* \* \* \* \*